US010893912B2

(12) United States Patent
Crawford et al.

(10) Patent No.: US 10,893,912 B2
(45) Date of Patent: *Jan. 19, 2021

(54) SURGICAL TOOL SYSTEMS AND METHODS

(71) Applicant: GLOBUS MEDICAL, INC., Audubon, PA (US)

(72) Inventors: Neil R. Crawford, Chandler, AZ (US); Nicholas A. Theodore, Paradise Valley, PA (US); Mitchell Foster, Scottsdale, AZ (US); Norbert Johnson, North Andover, MA (US); Timothy Moulton, Newport, RI (US); Kevin Zhang, Medford, MA (US); Jeffrey Forsyth, Cranston, RI (US); Chris Major, Philadelphia, PA (US); Robert LeBoeuf, Salem, MA (US); David Cleary, Somerville, MA (US)

(73) Assignee: Globus Medical Inc., Audubon, PA (US)

( * ) Notice: Subject to any disclaimer, the term of this patent is extended or adjusted under 35 U.S.C. 154(b) by 284 days.

This patent is subject to a terminal disclaimer.

(21) Appl. No.: 15/095,883

(22) Filed: Apr. 11, 2016

(65) Prior Publication Data

US 2016/0220320 A1 Aug. 4, 2016

Related U.S. Application Data

(63) Continuation-in-part of application No. 14/062,707, filed on Oct. 24, 2013, now Pat. No. 10,357,184, (Continued)

(51) Int. Cl.
A61B 34/30 (2016.01)
A61B 34/20 (2016.01)
(Continued)

(52) U.S. Cl.
CPC .............. *A61B 34/30* (2016.02); *A61B 5/064* (2013.01); *A61B 90/96* (2016.02); *A61B 90/98* (2016.02);
(Continued)

(58) Field of Classification Search
CPC .............. A61B 5/06; A61B 5/061–068; A61B 34/00–77; A61B 90/37
See application file for complete search history.

(56) References Cited

U.S. PATENT DOCUMENTS 4,150,293 A 4/1979 Franke
5,246,010 A 9/1993 Gazzara et al.
(Continued)

FOREIGN PATENT DOCUMENTS

EP 0744633 A2 11/1996
EP 2286729 A2 2/2011
(Continued)

OTHER PUBLICATIONS

US 8,231,638 B2, 07/2012, Swarup et al. (withdrawn)
(Continued)

*Primary Examiner* — Angela M Hoffa

(57) ABSTRACT

Embodiments of the present disclosure provide a surgical robot system may include an end-effector element configured for controlled movement and positioning and tracking of surgical instruments and objects relative to an image of a patient's anatomical structure. In some embodiments the end-effector may be tracked by surgical robot system and displayed to a user. In some embodiments the end-effector element may be configured to restrict the movement of an instrument assembly in a guide tube. In some embodiments, the end-effector may contain structures to allow for magnetic coupling to a robot arm and/or wireless powering of the end-effector element. In some embodiments, tracking of a
(Continued)

target anatomical structure and objects, both in a navigation space and an image space, may be provided by a dynamic reference base located at a position away from the target anatomical structure.

4 Claims, 20 Drawing Sheets

Related U.S. Application Data which is a continuation-in-part of application No. 13/924,505, filed on Jun. 21, 2013, now Pat. No. 9,782,229, application No. 15/095,883, which is a continuation-in-part of application No. 14/729,096, filed on Jun. 3, 2015, now Pat. No. 10,172,678, which is a continuation of application No. 13/542,560, filed on Jul. 5, 2012, now Pat. No. 9,078,685, which is a continuation of application No. 11/845,557, filed on Aug. 27, 2007, now Pat. No. 8,219,178, which is a continuation-in-part of application No. 11/838,027, filed on Aug. 13, 2007, now Pat. No. 8,219,177, which is a continuation-in-part of application No. 11/676,023, filed on Feb. 16, 2007, now Pat. No. 8,010,181.

(60) Provisional application No. 61/662,702, filed on Jun. 21, 2012, provisional application No. 61/800,527, filed on Mar. 15, 2013, provisional application No. 60/775,816, filed on Feb. 16, 2006, provisional application No. 60/774,586, filed on Feb. 16, 2006.

(51) Int. Cl.

| | | |
|---|---|---|
| *G06T 7/73* | (2017.01) | |
| *A61B 5/06* | (2006.01) | |
| *A61B 90/98* | (2016.01) | |
| *A61B 90/96* | (2016.01) | |
| *G06T 7/33* | (2017.01) | |
| *A61B 17/17* | (2006.01) | |
| *A61B 90/00* | (2016.01) | |
| *A61B 90/11* | (2016.01) | |
| *A61B 17/00* | (2006.01) | |

(52) U.S. Cl.
CPC ............... *G06T 7/73* (2017.01); *A61B 17/17* (2013.01); *A61B 90/11* (2016.02); *A61B 2017/00876* (2013.01); *A61B 2034/2051* (2016.02); *A61B 2034/2055* (2016.02); *A61B 2090/034* (2016.02); *A61B 2090/0811* (2016.02); *A61B 2090/3937* (2016.02); *A61B 2090/3945* (2016.02); *A61B 2560/0437* (2013.01); *G06T 7/33* (2017.01)

(56) References Cited

U.S. PATENT DOCUMENTS

| | | |
|---|---|---|
| 5,354,314 A | 10/1994 | Hardy et al. |
| 5,397,323 A | 3/1995 | Taylor et al. |
| 5,598,453 A | 1/1997 | Baba et al. |
| 5,772,594 A | 6/1998 | Barrick |
| 5,791,908 A | 8/1998 | Gillio |
| 5,820,559 A | 10/1998 | Ng et al. |
| 5,825,982 A | 10/1998 | Wright et al. |
| 5,887,121 A | 3/1999 | Funda et al. |
| 5,911,449 A | 6/1999 | Daniele et al. |
| 5,951,475 A | 9/1999 | Gueziec et al. |
| 5,987,960 A | 11/1999 | Messner et al. |
| 6,012,216 A | 1/2000 | Esteves et al. |
| 6,031,888 A | 2/2000 | Ivan et al. |
| 6,033,415 A | 3/2000 | Mittelstadt et al. |
| 6,080,181 A | 6/2000 | Jensen et al. |
| 6,106,511 A | 8/2000 | Jensen |
| 6,122,541 A | 9/2000 | Cosman et al. |
| 6,144,875 A | 11/2000 | Schweikard et al. |
| 6,157,853 A | 12/2000 | Blume et al. |
| 6,167,145 A | 12/2000 | Foley et al. |
| 6,167,292 A | 12/2000 | Badano et al. |
| 6,201,984 B1 | 3/2001 | Funda et al. |
| 6,203,196 B1 | 3/2001 | Meyer et al. |
| 6,205,411 B1 | 3/2001 | DiGioia, III et al. |
| 6,212,419 B1 | 4/2001 | Blume et al. |
| 6,231,565 B1 | 5/2001 | Tovey et al. |
| 6,236,875 B1 | 5/2001 | Bucholz et al. |
| 6,246,900 B1 | 6/2001 | Cosman et al. |
| 6,276,471 B1 | 8/2001 | Kratzenberg et al. |
| 6,301,495 B1 | 10/2001 | Gueziec et al. |
| 6,306,126 B1 | 10/2001 | Montezuma |
| 6,312,435 B1 | 11/2001 | Wallace et al. |
| 6,314,311 B1 | 11/2001 | Williams et al. |
| 6,320,929 B1 | 11/2001 | Von Der Haar |
| 6,322,567 B1 | 11/2001 | Mittelstadt et al. |
| 6,325,808 B1 | 12/2001 | Bernard et al. |
| 6,340,363 B1 | 1/2002 | Bolger et al. |
| 6,377,011 B1 | 4/2002 | Ben-Ur |
| 6,379,302 B1 | 4/2002 | Kessman et al. |
| 6,402,762 B2 | 6/2002 | Hunter et al. |
| 6,424,885 B1 | 7/2002 | Niemeyer et al. |
| 6,447,503 B1 | 9/2002 | Wynne et al. |
| 6,451,027 B1 | 9/2002 | Cooper et al. |
| 6,459,926 B1 * | 10/2002 | Nowlin ................. A61B 34/70 600/102 |
| 6,477,400 B1 | 11/2002 | Barrick |
| 6,484,049 B1 | 11/2002 | Seeley et al. |
| 6,487,267 B1 | 11/2002 | Wolter |
| 6,490,467 B1 | 12/2002 | Bucholz et al. |
| 6,490,475 B1 | 12/2002 | Seeley et al. |
| 6,499,488 B1 | 12/2002 | Hunter et al. |
| 6,501,981 B1 | 12/2002 | Schweikard et al. |
| 6,507,751 B2 | 1/2003 | Blume et al. |
| 6,535,756 B1 | 3/2003 | Simon et al. |
| 6,560,354 B1 | 5/2003 | Maurer, Jr. et al. |
| 6,565,554 B1 | 5/2003 | Niemeyer |
| 6,587,750 B2 | 7/2003 | Gerbi et al. |
| 6,614,453 B1 | 9/2003 | Suri et al. |
| 6,614,871 B1 | 9/2003 | Kobiki et al. |
| 6,619,840 B2 | 9/2003 | Rasche et al. |
| 6,636,757 B1 | 10/2003 | Jascob et al. |
| 6,645,196 B1 | 11/2003 | Nixon et al. |
| 6,666,579 B2 | 12/2003 | Jensen |
| 6,669,635 B2 | 12/2003 | Kessman et al. |
| 6,701,173 B2 | 3/2004 | Nowinski et al. |
| 6,757,068 B2 | 6/2004 | Foxlin |
| 6,782,287 B2 | 8/2004 | Grzeszczuk et al. |
| 6,783,524 B2 | 8/2004 | Anderson et al. |
| 6,786,896 B1 | 9/2004 | Madhani et al. |
| 6,788,018 B1 | 9/2004 | Blumenkranz |
| 6,804,581 B2 | 10/2004 | Wang et al. |
| 6,823,207 B1 | 11/2004 | Jensen et al. |
| 6,827,351 B2 | 12/2004 | Graziani et al. |
| 6,837,883 B2 * | 1/2005 | Moll ................. A61B 19/2203 606/1 |
| 6,837,892 B2 | 1/2005 | Shoham |
| 6,839,612 B2 | 1/2005 | Sanchez et al. |
| 6,856,826 B2 | 2/2005 | Seeley et al. |
| 6,856,827 B2 | 2/2005 | Seeley et al. |
| 6,879,880 B2 | 4/2005 | Nowlin et al. |
| 6,892,090 B2 | 5/2005 | Verard et al. |
| 6,920,347 B2 | 7/2005 | Simon et al. |
| 6,922,632 B2 | 7/2005 | Foxlin |
| 6,968,224 B2 | 11/2005 | Kessman et al. |
| 6,978,166 B2 | 12/2005 | Foley et al. |
| 6,988,009 B2 | 1/2006 | Grimm et al. |
| 6,991,627 B2 | 1/2006 | Madhani et al. |
| 6,996,487 B2 | 2/2006 | Jutras et al. |
| 6,999,852 B2 | 2/2006 | Green |
| 7,007,699 B2 | 3/2006 | Martinelli et al. |
| 7,016,457 B1 | 3/2006 | Senzig et al. |
| 7,043,961 B2 | 5/2006 | Pandey et al. |

(56) References Cited

U.S. PATENT DOCUMENTS

| | | |
|---|---|---|
| 7,062,006 B1 | 6/2006 | Pelc et al. |
| 7,063,705 B2 | 6/2006 | Young et al. |
| 7,072,707 B2 | 7/2006 | Galloway, Jr. et al. |
| 7,083,615 B2 | 8/2006 | Peterson et al. |
| 7,087,049 B2 * | 8/2006 | Nowlin .................. A61B 34/70 606/1 |
| 7,097,640 B2 | 8/2006 | Wang et al. |
| 7,099,428 B2 | 8/2006 | Clinthorne et al. |
| 7,108,421 B2 | 9/2006 | Gregerson et al. |
| 7,130,676 B2 | 10/2006 | Barrick |
| 7,139,418 B2 | 11/2006 | Abovitz et al. |
| 7,139,601 B2 | 11/2006 | Bucholz et al. |
| 7,155,316 B2 | 12/2006 | Sutherland et al. |
| 7,164,968 B2 | 1/2007 | Treat et al. |
| 7,167,738 B2 | 1/2007 | Schweikard et al. |
| 7,169,141 B2 | 1/2007 | Brock et al. |
| 7,172,627 B2 | 2/2007 | Fiere et al. |
| 7,194,120 B2 | 3/2007 | Wicker et al. |
| 7,197,107 B2 | 3/2007 | Arai et al. |
| 7,231,014 B2 | 6/2007 | Levy |
| 7,231,063 B2 | 6/2007 | Naimark et al. |
| 7,239,940 B2 | 7/2007 | Wang et al. |
| 7,248,914 B2 | 7/2007 | Hastings et al. |
| 7,301,648 B2 | 11/2007 | Foxlin |
| 7,302,288 B1 | 11/2007 | Schellenberg |
| 7,313,430 B2 | 12/2007 | Urquhart et al. |
| 7,318,805 B2 | 1/2008 | Schweikard et al. |
| 7,318,827 B2 | 1/2008 | Leitner et al. |
| 7,319,897 B2 | 1/2008 | Leitner et al. |
| 7,324,623 B2 | 1/2008 | Heuscher et al. |
| 7,327,865 B2 | 2/2008 | Fu et al. |
| 7,331,967 B2 | 2/2008 | Lee et al. |
| 7,333,642 B2 | 2/2008 | Green |
| 7,339,341 B2 | 3/2008 | Oleynikov et al. |
| 7,366,562 B2 | 4/2008 | Dukesherer et al. |
| 7,379,790 B2 * | 5/2008 | Toth ........................ G16H 40/40 700/245 |
| 7,386,365 B2 | 6/2008 | Nixon |
| 7,422,592 B2 | 9/2008 | Morley et al. |
| 7,435,216 B2 | 10/2008 | Kwon et al. |
| 7,440,793 B2 | 10/2008 | Chauhan et al. |
| 7,460,637 B2 | 12/2008 | Clinthorne et al. |
| 7,466,303 B2 | 12/2008 | Yi et al. |
| 7,493,153 B2 | 2/2009 | Ahmed et al. |
| 7,505,617 B2 | 3/2009 | Fu et al. |
| 7,533,892 B2 | 5/2009 | Schena et al. |
| 7,542,791 B2 | 6/2009 | Mire et al. |
| 7,555,331 B2 | 6/2009 | Viswanathan |
| 7,567,834 B2 | 7/2009 | Clayton et al. |
| 7,594,912 B2 | 9/2009 | Cooper et al. |
| 7,606,613 B2 | 10/2009 | Simon et al. |
| 7,607,440 B2 | 10/2009 | Coste-Maniere et al. |
| 7,623,902 B2 | 11/2009 | Pacheco |
| 7,630,752 B2 | 12/2009 | Viswanathan |
| 7,630,753 B2 | 12/2009 | Simon et al. |
| 7,643,862 B2 | 1/2010 | Schoenefeld |
| 7,660,623 B2 | 2/2010 | Hunter et al. |
| 7,661,881 B2 | 2/2010 | Gregerson et al. |
| 7,683,331 B2 | 3/2010 | Chang |
| 7,683,332 B2 | 3/2010 | Chang |
| 7,689,320 B2 | 3/2010 | Prisco et al. |
| 7,691,098 B2 | 4/2010 | Wallace et al. |
| 7,702,379 B2 | 4/2010 | Avinash et al. |
| 7,702,477 B2 | 4/2010 | Tuemmler et al. |
| 7,711,083 B2 | 5/2010 | Heigl et al. |
| 7,711,406 B2 | 5/2010 | Kuhn et al. |
| 7,720,523 B2 | 5/2010 | Omernick et al. |
| 7,725,253 B2 | 5/2010 | Foxlin |
| 7,726,171 B2 | 6/2010 | Langlotz et al. |
| 7,742,801 B2 | 6/2010 | Neubauer et al. |
| 7,751,865 B2 | 7/2010 | Jascob et al. |
| 7,760,849 B2 | 7/2010 | Zhang |
| 7,762,825 B2 | 7/2010 | Burbank et al. |
| 7,763,015 B2 | 7/2010 | Cooper et al. |
| 7,787,699 B2 | 8/2010 | Mahesh et al. |
| 7,796,728 B2 | 9/2010 | Bergfjord |
| 7,806,891 B2 * | 10/2010 | Nowlin .................. A61B 34/70 128/898 |
| 7,813,838 B2 | 10/2010 | Sommer |
| 7,818,044 B2 | 10/2010 | Dukesherer et al. |
| 7,819,859 B2 | 10/2010 | Prisco et al. |
| 7,824,401 B2 | 11/2010 | Manzo et al. |
| 7,831,294 B2 | 11/2010 | Viswanathan |
| 7,834,484 B2 | 11/2010 | Sartor |
| 7,835,557 B2 | 11/2010 | Kendrick et al. |
| 7,835,778 B2 | 11/2010 | Foley et al. |
| 7,835,784 B2 | 11/2010 | Mire et al. |
| 7,840,253 B2 | 11/2010 | Tremblay et al. |
| 7,840,256 B2 | 11/2010 | Lakin et al. |
| 7,843,158 B2 | 11/2010 | Prisco |
| 7,844,320 B2 | 11/2010 | Shahidi |
| 7,853,305 B2 | 12/2010 | Simon et al. |
| 7,853,313 B2 | 12/2010 | Thompson |
| 7,865,269 B2 | 1/2011 | Prisco et al. |
| D631,966 S | 2/2011 | Perloff et al. |
| 7,879,045 B2 | 2/2011 | Gielen et al. |
| 7,881,767 B2 | 2/2011 | Strommer et al. |
| 7,881,770 B2 | 2/2011 | Melkent et al. |
| 7,886,743 B2 | 2/2011 | Cooper et al. |
| RE42,194 E | 3/2011 | Foley et al. |
| RE42,226 E | 3/2011 | Foley et al. |
| 7,900,524 B2 | 3/2011 | Calloway et al. |
| 7,907,166 B2 | 3/2011 | Lamprecht et al. |
| 7,909,122 B2 | 3/2011 | Schena et al. |
| 7,925,653 B2 | 4/2011 | Saptharishi |
| 7,930,065 B2 | 4/2011 | Larkin et al. |
| 7,935,130 B2 | 5/2011 | Willliams |
| 7,940,999 B2 | 5/2011 | Liao et al. |
| 7,945,012 B2 | 5/2011 | Ye et al. |
| 7,945,021 B2 | 5/2011 | Shapiro et al. |
| 7,953,470 B2 | 5/2011 | Vetter et al. |
| 7,954,397 B2 | 6/2011 | Choi et al. |
| 7,971,341 B2 | 7/2011 | Dukesherer et al. |
| 7,974,674 B2 | 7/2011 | Hauck et al. |
| 7,974,677 B2 | 7/2011 | Mire et al. |
| 7,974,681 B2 | 7/2011 | Wallace et al. |
| 7,979,157 B2 | 7/2011 | Anvari |
| 7,983,733 B2 | 7/2011 | Viswanathan |
| 7,983,793 B2 * | 7/2011 | Toth ........................ G16H 40/40 700/245 |
| 7,988,215 B2 | 8/2011 | Seibold |
| 7,996,110 B2 | 8/2011 | Lipow et al. |
| 8,004,121 B2 | 8/2011 | Sartor |
| 8,004,229 B2 | 8/2011 | Nowlin et al. |
| 8,010,177 B2 | 8/2011 | Csavoy et al. |
| 8,010,180 B2 * | 8/2011 | Quaid .................... A61N 1/372 600/424 |
| 8,010,181 B2 * | 8/2011 | Smith ...................... A61B 5/06 600/411 |
| 8,019,045 B2 | 9/2011 | Kato |
| 8,021,310 B2 | 9/2011 | Sanborn et al. |
| 8,035,685 B2 | 10/2011 | Jensen |
| 8,046,054 B2 | 10/2011 | Kim et al. |
| 8,046,057 B2 | 10/2011 | Clarke |
| 8,052,688 B2 | 11/2011 | Wolf, II |
| 8,054,184 B2 | 11/2011 | Cline et al. |
| 8,054,752 B2 | 11/2011 | Druke et al. |
| 8,057,397 B2 | 11/2011 | Li et al. |
| 8,057,407 B2 | 11/2011 | Martinelli et al. |
| 8,062,288 B2 | 11/2011 | Cooper et al. |
| 8,062,375 B2 | 11/2011 | Glerum et al. |
| 8,066,524 B2 | 11/2011 | Burbank et al. |
| 8,073,335 B2 | 12/2011 | Labonville et al. |
| 8,079,950 B2 | 12/2011 | Stern et al. |
| 8,086,299 B2 | 12/2011 | Adler et al. |
| 8,092,370 B2 | 1/2012 | Roberts et al. |
| 8,098,914 B2 | 1/2012 | Liao et al. |
| 8,100,950 B2 | 1/2012 | St. Clair et al. |
| 8,105,320 B2 | 1/2012 | Manzo |
| 8,108,025 B2 | 1/2012 | Csavoy et al. |
| 8,109,877 B2 | 2/2012 | Moctezuma de la Barrera et al. |
| 8,112,292 B2 | 2/2012 | Simon |
| 8,116,430 B1 | 2/2012 | Shapiro et al. |
| 8,120,301 B2 | 2/2012 | Goldberg et al. |

(56) References Cited

U.S. PATENT DOCUMENTS

| | | |
|---|---|---|
| 8,121,249 B2 | 2/2012 | Wang et al. |
| 8,123,675 B2 | 2/2012 | Funda et al. |
| 8,133,229 B1 | 3/2012 | Bonutti |
| 8,142,420 B2 | 3/2012 | Schena |
| 8,147,494 B2 | 4/2012 | Leitner et al. |
| 8,150,494 B2 | 4/2012 | Simon et al. |
| 8,150,497 B2 | 4/2012 | Gielen et al. |
| 8,150,498 B2 | 4/2012 | Gielen et al. |
| 8,165,658 B2 | 4/2012 | Waynik et al. |
| 8,170,313 B2 | 5/2012 | Kendrick et al. |
| 8,179,073 B2 | 5/2012 | Farritor et al. |
| 8,182,476 B2 | 5/2012 | Julian et al. |
| 8,182,491 B2 * | 5/2012 | Selover .............. A61B 90/13 606/104 |
| 8,184,880 B2 | 5/2012 | Zhao et al. |
| 8,202,278 B2 | 6/2012 | Orban, III et al. |
| 8,208,708 B2 | 6/2012 | Homan et al. |
| 8,208,988 B2 | 6/2012 | Jensen |
| 8,219,177 B2 * | 7/2012 | Smith .............. A61B 5/06 600/411 |
| 8,219,178 B2 * | 7/2012 | Smith .............. A61B 5/06 600/424 |
| 8,220,468 B2 | 7/2012 | Cooper et al. |
| 8,224,024 B2 | 7/2012 | Foxlin et al. |
| 8,224,484 B2 | 7/2012 | Swarup et al. |
| 8,225,798 B2 | 7/2012 | Baldwin et al. |
| 8,228,368 B2 | 7/2012 | Zhao et al. |
| 8,231,610 B2 | 7/2012 | Jo et al. |
| 8,263,933 B2 | 7/2012 | Hartmann et al. |
| 8,239,001 B2 | 8/2012 | Verard et al. |
| 8,241,271 B2 | 8/2012 | Millman et al. |
| 8,248,413 B2 | 8/2012 | Gattani et al. |
| 8,256,319 B2 | 9/2012 | Cooper et al. |
| 8,271,069 B2 | 9/2012 | Jascob et al. |
| 8,271,130 B2 | 9/2012 | Hourtash |
| 8,281,670 B2 | 10/2012 | Larkin et al. |
| 8,282,653 B2 | 10/2012 | Nelson et al. |
| 8,301,226 B2 | 10/2012 | Csavoy et al. |
| 8,311,611 B2 | 11/2012 | Csavoy et al. |
| 8,320,991 B2 | 11/2012 | Jascob et al. |
| 8,332,012 B2 | 12/2012 | Kienzle, III |
| 8,333,755 B2 | 12/2012 | Cooper et al. |
| 8,335,552 B2 | 12/2012 | Stiles |
| 8,335,557 B2 | 12/2012 | Maschke |
| 8,348,931 B2 | 1/2013 | Cooper et al. |
| 8,353,963 B2 | 1/2013 | Glerum |
| 8,358,818 B2 | 1/2013 | Miga et al. |
| 8,359,730 B2 | 1/2013 | Burg et al. |
| 8,374,673 B2 | 2/2013 | Adcox et al. |
| 8,374,723 B2 | 2/2013 | Zhao et al. |
| 8,379,791 B2 | 2/2013 | Forthmann et al. |
| 8,386,019 B2 | 2/2013 | Camus et al. |
| 8,392,022 B2 | 3/2013 | Ortmaier et al. |
| 8,394,099 B2 | 3/2013 | Patwardhan |
| 8,395,342 B2 | 3/2013 | Prisco |
| 8,398,634 B2 | 3/2013 | Manzo et al. |
| 8,400,094 B2 | 3/2013 | Schena |
| 8,414,957 B2 | 4/2013 | Enzerink et al. |
| 8,418,073 B2 | 4/2013 | Mohr et al. |
| 8,450,694 B2 | 5/2013 | Baviera et al. |
| 8,452,447 B2 | 5/2013 | Nixon |
| RE44,305 E | 6/2013 | Foley et al. |
| 8,462,911 B2 | 6/2013 | Vesel et al. |
| 8,465,476 B2 | 6/2013 | Rogers et al. |
| 8,465,771 B2 | 6/2013 | Wan et al. |
| 8,467,851 B2 | 6/2013 | Mire et al. |
| 8,467,852 B2 | 6/2013 | Csavoy et al. |
| 8,469,947 B2 | 6/2013 | Devengenzo et al. |
| RE44,392 E | 7/2013 | Hynes |
| 8,483,434 B2 | 7/2013 | Buehner et al. |
| 8,483,800 B2 | 7/2013 | Jensen et al. |
| 8,486,532 B2 | 7/2013 | Enzerink et al. |
| 8,489,235 B2 | 7/2013 | Moll et al. |
| 8,500,722 B2 | 8/2013 | Cooper |
| 8,500,728 B2 | 8/2013 | Newton et al. |
| 8,504,201 B2 | 8/2013 | Moll et al. |
| 8,506,555 B2 | 8/2013 | Ruiz Morales |
| 8,506,556 B2 | 8/2013 | Schena |
| 8,508,173 B2 | 8/2013 | Goldberg et al. |
| 8,512,318 B2 | 8/2013 | Tovey et al. |
| 8,515,576 B2 | 8/2013 | Lipow et al. |
| 8,518,120 B2 | 8/2013 | Glerum et al. |
| 8,521,331 B2 | 8/2013 | Itkowitz |
| 8,526,688 B2 | 9/2013 | Groszmann et al. |
| 8,526,700 B2 | 9/2013 | Isaacs |
| 8,527,094 B2 | 9/2013 | Kumar et al. |
| 8,528,440 B2 | 9/2013 | Morley et al. |
| 8,532,741 B2 | 9/2013 | Heruth et al. |
| 8,541,970 B2 | 9/2013 | Nowlin et al. |
| 8,548,563 B2 | 10/2013 | Simon et al. |
| 8,549,732 B2 | 10/2013 | Burg et al. |
| 8,551,114 B2 | 10/2013 | Ramos de la Pena |
| 8,551,116 B2 | 10/2013 | Julian et al. |
| 8,556,807 B2 | 10/2013 | Scott et al. |
| 8,556,979 B2 | 10/2013 | Glerum et al. |
| 8,560,118 B2 | 10/2013 | Green et al. |
| 8,561,473 B2 | 10/2013 | Blumenkranz |
| 8,562,594 B2 | 10/2013 | Cooper et al. |
| 8,571,638 B2 | 10/2013 | Shoham |
| 8,571,710 B2 | 10/2013 | Coste-Maniere et al. |
| 8,573,465 B2 | 11/2013 | Shelton, IV |
| 8,574,303 B2 | 11/2013 | Sharkey et al. |
| 8,585,420 B2 | 11/2013 | Burbank et al. |
| 8,594,841 B2 | 11/2013 | Zhao et al. |
| 8,597,198 B2 | 12/2013 | Sanborn et al. |
| 8,600,478 B2 | 12/2013 | Verard et al. |
| 8,600,551 B2 * | 12/2013 | Itkowitz .............. G09B 23/285 700/245 |
| 8,603,077 B2 | 12/2013 | Cooper et al. |
| 8,611,985 B2 | 12/2013 | Lavallee et al. |
| 8,613,230 B2 | 12/2013 | Blumenkranz et al. |
| 8,621,939 B2 | 1/2014 | Blumenkranz et al. |
| 8,624,537 B2 | 1/2014 | Nowlin et al. |
| 8,630,389 B2 | 1/2014 | Kato |
| 8,634,897 B2 | 1/2014 | Simon et al. |
| 8,634,957 B2 * | 1/2014 | Toth .............. G16H 40/40 700/245 |
| 8,638,056 B2 | 1/2014 | Goldberg et al. |
| 8,638,057 B2 | 1/2014 | Goldberg et al. |
| 8,639,000 B2 | 1/2014 | Zhao et al. |
| 8,641,726 B2 | 2/2014 | Bonutti |
| 8,644,907 B2 | 2/2014 | Hartmann et al. |
| 8,657,809 B2 | 2/2014 | Schoepp |
| 8,660,635 B2 | 2/2014 | Simon et al. |
| 8,666,544 B2 | 3/2014 | Moll et al. |
| 8,675,939 B2 | 3/2014 | Moctezuma de la Barrera |
| 8,678,647 B2 | 3/2014 | Gregerson et al. |
| 8,679,125 B2 | 3/2014 | Smith et al. |
| 8,679,183 B2 | 3/2014 | Glerum et al. |
| 8,682,413 B2 | 3/2014 | Lloyd |
| 8,684,253 B2 | 4/2014 | Giordano et al. |
| 8,685,098 B2 | 4/2014 | Glerum et al. |
| 8,693,730 B2 | 4/2014 | Umasuthan et al. |
| 8,694,075 B2 | 4/2014 | Groszmann et al. |
| 8,696,458 B2 | 4/2014 | Foxlin et al. |
| 8,700,123 B2 | 4/2014 | Okamura et al. |
| 8,706,086 B2 | 4/2014 | Glerum |
| 8,706,185 B2 | 4/2014 | Foley et al. |
| 8,706,301 B2 | 4/2014 | Zhao et al. |
| 8,717,430 B2 | 5/2014 | Simon et al. |
| 8,727,618 B2 | 5/2014 | Maschke et al. |
| 8,734,432 B2 | 5/2014 | Tuma et al. |
| 8,738,115 B2 | 5/2014 | Amberg et al. |
| 8,738,181 B2 | 5/2014 | Greer et al. |
| 8,740,882 B2 | 6/2014 | Jun et al. |
| 8,746,252 B2 | 6/2014 | McGrogan et al. |
| 8,747,238 B2 * | 6/2014 | Shelton, IV .............. B23K 26/38 464/149 |
| 8,749,189 B2 | 6/2014 | Nowlin et al. |
| 8,749,190 B2 | 6/2014 | Nowlin et al. |
| 8,761,930 B2 | 6/2014 | Nixon |
| 8,764,448 B2 | 7/2014 | Yang et al. |
| 8,771,170 B2 | 7/2014 | Mesallum et al. |
| 8,781,186 B2 | 7/2014 | Clements et al. |

(56) References Cited

U.S. PATENT DOCUMENTS

| | | |
|---|---|---|
| 8,781,630 B2 | 7/2014 | Banks et al. |
| 8,784,385 B2 | 7/2014 | Boyden et al. |
| 8,786,241 B2 | 7/2014 | Nowlin et al. |
| 8,787,520 B2 | 7/2014 | Baba |
| 8,792,704 B2 | 7/2014 | Isaacs |
| 8,798,231 B2 | 8/2014 | Notohara et al. |
| 8,800,838 B2 | 8/2014 | Shelton, IV |
| 8,808,164 B2 | 8/2014 | Hoffman et al. |
| 8,812,077 B2 | 8/2014 | Dempsey |
| 8,814,793 B2 | 8/2014 | Brabrand |
| 8,816,628 B2 | 8/2014 | Nowlin et al. |
| 8,818,105 B2 | 8/2014 | Myronenko et al. |
| 8,820,605 B2 | 9/2014 | Shelton, IV |
| 8,821,511 B2 | 9/2014 | Von Jako et al. |
| 8,823,308 B2 | 9/2014 | Nowlin et al. |
| 8,827,996 B2 | 9/2014 | Scott et al. |
| 8,828,024 B2 | 9/2014 | Farritor et al. |
| 8,830,224 B2 | 9/2014 | Zhao et al. |
| 8,834,489 B2 | 9/2014 | Cooper et al. |
| 8,834,490 B2 | 9/2014 | Bonutti |
| 8,838,270 B2 | 9/2014 | Druke et al. |
| 8,844,789 B2 | 9/2014 | Shelton, IV et al. |
| 8,855,822 B2 | 10/2014 | Bartol et al. |
| 8,858,598 B2 | 10/2014 | Seifert et al. |
| 8,860,753 B2 | 10/2014 | Bhandarkar et al. |
| 8,864,751 B2 | 10/2014 | Prisco et al. |
| 8,864,798 B2 | 10/2014 | Weiman et al. |
| 8,864,833 B2 | 10/2014 | Glerum et al. |
| 8,867,703 B2 | 10/2014 | Shapiro et al. |
| 8,870,880 B2 | 10/2014 | Himmelberger et al. |
| 8,876,866 B2 | 11/2014 | Zappacosta et al. |
| 8,880,223 B2 | 11/2014 | Raj et al. |
| 8,882,803 B2 | 11/2014 | Iott et al. |
| 8,883,210 B1 | 11/2014 | Truncale et al. |
| 8,888,821 B2 | 11/2014 | Rezach et al. |
| 8,888,853 B2 | 11/2014 | Glerum et al. |
| 8,888,854 B2 | 11/2014 | Glerum et al. |
| 8,894,652 B2 | 11/2014 | Seifert et al. |
| 8,894,688 B2 | 11/2014 | Suh |
| 8,894,691 B2 | 11/2014 | Iott et al. |
| 8,906,069 B2 | 12/2014 | Hansell et al. |
| 8,964,934 B2 | 2/2015 | Ein-Gal |
| 8,992,580 B2 | 3/2015 | Bar et al. |
| 8,996,169 B2 | 3/2015 | Lightcap et al. |
| 9,001,963 B2 | 4/2015 | Sowards-Emmerd et al. |
| 9,002,076 B2 | 4/2015 | Khadem et al. |
| 9,044,190 B2 | 6/2015 | Rubner et al. |
| 9,072,536 B2* | 7/2015 | Shelton, IV ....... A61B 19/2203 |
| 9,078,685 B2* | 7/2015 | Smith ...................... A61B 5/06 |
| 9,107,683 B2 | 8/2015 | Hourtash et al. |
| 9,125,556 B2 | 9/2015 | Zehavi et al. |
| 9,131,986 B2 | 9/2015 | Greer et al. |
| 9,215,968 B2 | 12/2015 | Schostek et al. |
| 9,226,751 B2* | 1/2016 | Shelton, IV ..... A61B 17/07207 |
| 9,308,050 B2 | 4/2016 | Kostrzewski et al. |
| 9,345,546 B2* | 5/2016 | Toth ...................... G16H 40/40 |
| 9,364,230 B2* | 6/2016 | Shelton, IV ..... A61B 17/07207 |
| 9,380,984 B2 | 7/2016 | Li et al. |
| 9,393,039 B2 | 7/2016 | Lechner et al. |
| 9,398,886 B2 | 7/2016 | Gregerson et al. |
| 9,398,890 B2 | 7/2016 | Dong et al. |
| 9,408,606 B2* | 8/2016 | Shelton, IV ..... A61B 17/07207 |
| 9,414,859 B2 | 8/2016 | Ballard et al. |
| 9,420,975 B2 | 8/2016 | Gutfleisch et al. |
| 9,492,097 B2* | 11/2016 | Wilkes ................... A61B 5/042 |
| 9,492,235 B2 | 11/2016 | Hourtash et al. |
| 9,504,527 B2* | 11/2016 | Smaby ................... A61B 34/30 |
| 9,592,096 B2 | 3/2017 | Maillet et al. |
| 9,750,465 B2 | 9/2017 | Engel et al. |
| 9,757,203 B2 | 9/2017 | Hourtash et al. |
| 9,782,229 B2* | 10/2017 | Crawford ............... A61B 34/30 |
| 9,782,230 B2* | 10/2017 | Smaby ................... A61B 34/30 |
| 9,795,354 B2 | 10/2017 | Menegaz et al. |
| 9,814,535 B2 | 11/2017 | Bar et al. |
| 9,820,783 B2 | 11/2017 | Donner et al. |
| 9,833,265 B2 | 11/2017 | Donner et al. |
| 9,848,922 B2 | 12/2017 | Tohmeh et al. |
| 9,925,011 B2 | 3/2018 | Gombert et al. |
| 9,931,025 B1 | 4/2018 | Graetzel et al. |
| 10,034,717 B2 | 7/2018 | Miller et al. |
| 2001/0036302 A1 | 11/2001 | Miller |
| 2002/0035321 A1 | 3/2002 | Bucholz et al. |
| 2002/0128552 A1* | 9/2002 | Nowlin .................. A61B 34/70 600/427 |
| 2003/0055049 A1 | 3/2003 | Brock |
| 2003/0153829 A1 | 8/2003 | Sarin et al. |
| 2004/0068172 A1 | 4/2004 | Nowinski et al. |
| 2004/0076259 A1 | 4/2004 | Jensen et al. |
| 2005/0096502 A1 | 5/2005 | Khalili |
| 2005/0143651 A1 | 6/2005 | Verard et al. |
| 2005/0171558 A1 | 8/2005 | Abovitz et al. |
| 2005/0245820 A1 | 11/2005 | Sarin |
| 2005/0251156 A1* | 11/2005 | Toth ........................ G16H 40/40 606/153 |
| 2006/0100610 A1 | 5/2006 | Wallace et al. |
| 2006/0142657 A1* | 6/2006 | Quaid ................ A61B 17/1764 600/424 |
| 2006/0173329 A1 | 8/2006 | Marquart et al. |
| 2006/0184396 A1 | 8/2006 | Dennis et al. |
| 2006/0241414 A1* | 10/2006 | Nowlin .................. A61B 34/70 600/431 |
| 2006/0241416 A1 | 10/2006 | Marquart et al. |
| 2006/0291612 A1 | 12/2006 | Nishide et al. |
| 2007/0015987 A1 | 1/2007 | Benlloch Baviera et al. |
| 2007/0021738 A1 | 1/2007 | Hasser et al. |
| 2007/0038059 A1 | 2/2007 | Sheffer et al. |
| 2007/0073133 A1 | 3/2007 | Schoenefeld |
| 2007/0156121 A1 | 7/2007 | Millman et al. |
| 2007/0156157 A1 | 7/2007 | Nahum et al. |
| 2007/0167712 A1 | 7/2007 | Keglovich et al. |
| 2007/0233238 A1 | 10/2007 | Huynh et al. |
| 2007/0238985 A1* | 10/2007 | Smith ...................... A61B 5/06 600/424 |
| 2008/0004523 A1 | 1/2008 | Jensen |
| 2008/0013809 A1 | 1/2008 | Zhu et al. |
| 2008/0033283 A1 | 2/2008 | Dellaca et al. |
| 2008/0046122 A1 | 2/2008 | Manzo et al. |
| 2008/0082109 A1 | 4/2008 | Moll et al. |
| 2008/0108912 A1 | 5/2008 | Node-Langlois |
| 2008/0108991 A1 | 5/2008 | Von Jako |
| 2008/0109012 A1 | 5/2008 | Falco et al. |
| 2008/0144906 A1 | 6/2008 | Allred et al. |
| 2008/0161680 A1 | 7/2008 | Von Jako et al. |
| 2008/0161682 A1 | 7/2008 | Kendrick et al. |
| 2008/0177203 A1 | 7/2008 | von Jako |
| 2008/0214922 A1 | 9/2008 | Hartmann et al. |
| 2008/0215181 A1* | 9/2008 | Smith ...................... A61B 5/06 700/245 |
| 2008/0221732 A1* | 9/2008 | Toth ........................ G16H 40/40 700/245 |
| 2008/0228068 A1 | 9/2008 | Viswanathan et al. |
| 2008/0228196 A1 | 9/2008 | Wang et al. |
| 2008/0235052 A1 | 9/2008 | Node-Langlois et al. |
| 2008/0269596 A1 | 10/2008 | Revie et al. |
| 2008/0287771 A1 | 11/2008 | Anderson |
| 2008/0287781 A1 | 11/2008 | Revie et al. |
| 2008/0300477 A1 | 12/2008 | Lloyd et al. |
| 2008/0300478 A1 | 12/2008 | Zuhars et al. |
| 2008/0302950 A1 | 12/2008 | Park et al. |
| 2008/0306490 A1 | 12/2008 | Lakin et al. |
| 2008/0319311 A1 | 12/2008 | Hamadeh |
| 2009/0012509 A1 | 1/2009 | Csavoy et al. |
| 2009/0030428 A1 | 1/2009 | Omori et al. |
| 2009/0080737 A1 | 3/2009 | Battle et al. |
| 2009/0185655 A1 | 7/2009 | Koken et al. |
| 2009/0198121 A1 | 8/2009 | Hoheisel |
| 2009/0216113 A1 | 8/2009 | Meier et al. |
| 2009/0228019 A1 | 9/2009 | Gross et al. |
| 2009/0259123 A1 | 10/2009 | Navab et al. |
| 2009/0259230 A1 | 10/2009 | Khadem et al. |
| 2009/0264899 A1 | 10/2009 | Appenrodt et al. |
| 2009/0281417 A1 | 11/2009 | Hartmann et al. |
| 2010/0022874 A1 | 1/2010 | Wang et al. |
| 2010/0039506 A1 | 2/2010 | Sarvestani et al. |

(56) References Cited

U.S. PATENT DOCUMENTS

| | | |
|---|---|---|
| 2010/0125286 A1 | 5/2010 | Wang et al. |
| 2010/0130986 A1 | 5/2010 | Mailloux et al. |
| 2010/0228117 A1 | 9/2010 | Hartmann |
| 2010/0228264 A1* | 9/2010 | Robinson ............ A61B 18/1206 606/130 |
| 2010/0228265 A1 | 9/2010 | Prisco |
| 2010/0234857 A1* | 9/2010 | Itkowitz ............... G09B 23/285 606/130 |
| 2010/0249571 A1 | 9/2010 | Jensen et al. |
| 2010/0274120 A1 | 10/2010 | Heuscher |
| 2010/0280363 A1 | 11/2010 | Skarda et al. |
| 2010/0331858 A1 | 12/2010 | Simaan et al. |
| 2011/0022229 A1 | 1/2011 | Jang et al. |
| 2011/0077504 A1 | 3/2011 | Fischer et al. |
| 2011/0098553 A1 | 4/2011 | Robbins et al. |
| 2011/0137152 A1 | 6/2011 | Li |
| 2011/0213384 A1 | 9/2011 | Jeong |
| 2011/0224684 A1 | 9/2011 | Larkin et al. |
| 2011/0224685 A1 | 9/2011 | Larkin et al. |
| 2011/0224686 A1 | 9/2011 | Larkin et al. |
| 2011/0224687 A1 | 9/2011 | Larkin et al. |
| 2011/0224688 A1 | 9/2011 | Larkin et al. |
| 2011/0224689 A1 | 9/2011 | Larkin et al. |
| 2011/0224825 A1 | 9/2011 | Larkin et al. |
| 2011/0230967 A1 | 9/2011 | O'Halloran et al. |
| 2011/0238080 A1 | 9/2011 | Ranjit et al. |
| 2011/0276058 A1 | 11/2011 | Choi et al. |
| 2011/0282189 A1 | 11/2011 | Graumann |
| 2011/0286573 A1 | 11/2011 | Schretter et al. |
| 2011/0295062 A1 | 12/2011 | Gratacos Solsona et al. |
| 2011/0295370 A1 | 12/2011 | Suh et al. |
| 2011/0301754 A1* | 12/2011 | Toth ........................ G16H 40/40 700/245 |
| 2011/0306986 A1 | 12/2011 | Lee et al. |
| 2012/0035507 A1 | 2/2012 | George et al. |
| 2012/0046668 A1 | 2/2012 | Gantes |
| 2012/0051498 A1 | 3/2012 | Koishi |
| 2012/0053597 A1 | 3/2012 | Anvari et al. |
| 2012/0059248 A1 | 3/2012 | Holsing et al. |
| 2012/0071753 A1 | 3/2012 | Hunter et al. |
| 2012/0108954 A1 | 5/2012 | Schulhauser et al. |
| 2012/0109150 A1* | 5/2012 | Quaid ................. A61B 17/1764 606/130 |
| 2012/0136372 A1 | 5/2012 | Amat Girbau et al. |
| 2012/0143084 A1 | 6/2012 | Shoham |
| 2012/0184839 A1 | 7/2012 | Woerlein |
| 2012/0197182 A1 | 8/2012 | Millman et al. |
| 2012/0226145 A1* | 9/2012 | Chang .................... A61B 34/30 600/424 |
| 2012/0235909 A1 | 9/2012 | Birkenbach et al. |
| 2012/0245596 A1 | 9/2012 | Meenink |
| 2012/0253332 A1 | 10/2012 | Moll |
| 2012/0253360 A1 | 10/2012 | White et al. |
| 2012/0256092 A1 | 10/2012 | Zingerman |
| 2012/0294498 A1 | 11/2012 | Popovic |
| 2012/0296203 A1 | 11/2012 | Hartmann et al. |
| 2013/0006267 A1 | 1/2013 | Odermatt et al. |
| 2013/0016889 A1 | 1/2013 | Myronenko et al. |
| 2013/0030571 A1 | 1/2013 | Ruiz Morales et al. |
| 2013/0035583 A1 | 2/2013 | Park et al. |
| 2013/0060146 A1 | 3/2013 | Yang et al. |
| 2013/0060337 A1 | 3/2013 | Petersheim et al. |
| 2013/0094742 A1 | 4/2013 | Feilkas |
| 2013/0096574 A1 | 4/2013 | Kang et al. |
| 2013/0113791 A1 | 5/2013 | Isaacs et al. |
| 2013/0116706 A1 | 5/2013 | Lee et al. |
| 2013/0131695 A1 | 5/2013 | Scarfogliero et al. |
| 2013/0144307 A1 | 6/2013 | Jeong et al. |
| 2013/0158542 A1 | 6/2013 | Manzo et al. |
| 2013/0165937 A1 | 6/2013 | Patwardhan |
| 2013/0178867 A1 | 7/2013 | Farritor et al. |
| 2013/0178868 A1 | 7/2013 | Roh |
| 2013/0178870 A1 | 7/2013 | Schena |
| 2013/0204271 A1 | 8/2013 | Brisson et al. |
| 2013/0211419 A1 | 8/2013 | Jensen |
| 2013/0211420 A1 | 8/2013 | Jensen |
| 2013/0218142 A1 | 8/2013 | Tuma et al. |
| 2013/0223702 A1 | 8/2013 | Holsing et al. |
| 2013/0225942 A1 | 8/2013 | Holsing et al. |
| 2013/0225943 A1 | 8/2013 | Holsing et al. |
| 2013/0231556 A1 | 9/2013 | Holsing et al. |
| 2013/0237995 A1 | 9/2013 | Lee et al. |
| 2013/0245375 A1 | 9/2013 | DiMaio et al. |
| 2013/0261640 A1 | 10/2013 | Kim et al. |
| 2013/0272488 A1 | 10/2013 | Bailey et al. |
| 2013/0272489 A1 | 10/2013 | Dickman et al. |
| 2013/0274761 A1 | 10/2013 | Devengenzo et al. |
| 2013/0281821 A1 | 10/2013 | Liu et al. |
| 2013/0296884 A1 | 11/2013 | Taylor et al. |
| 2013/0303887 A1 | 11/2013 | Holsing et al. |
| 2013/0307955 A1 | 11/2013 | Deitz et al. |
| 2013/0317521 A1 | 11/2013 | Choi et al. |
| 2013/0325033 A1 | 12/2013 | Schena et al. |
| 2013/0325035 A1 | 12/2013 | Hauck et al. |
| 2013/0331686 A1 | 12/2013 | Freysinger et al. |
| 2013/0331858 A1 | 12/2013 | Devengenzo et al. |
| 2013/0331861 A1 | 12/2013 | Yoon |
| 2013/0342578 A1 | 12/2013 | Isaacs |
| 2013/0345717 A1 | 12/2013 | Markvicka et al. |
| 2013/0345718 A1* | 12/2013 | Crawford ............. A61B 17/025 606/130 |
| 2013/0345757 A1 | 12/2013 | Stad |
| 2014/0000411 A1* | 1/2014 | Shelton, IV ........ A61B 19/2203 74/650 |
| 2014/0001231 A1* | 1/2014 | Shelton, IV ...... A61B 17/07207 227/175.3 |
| 2014/0001234 A1* | 1/2014 | Shelton, IV ...... A61B 17/07207 227/176.1 |
| 2014/0001235 A1* | 1/2014 | Shelton, IV ...... A61B 17/07207 227/176.1 |
| 2014/0001236 A1* | 1/2014 | Shelton, IV ...... A61B 17/07207 227/176.1 |
| 2014/0005677 A1* | 1/2014 | Shelton, IV ............. B23K 26/38 606/130 |
| 2014/0005678 A1* | 1/2014 | Shelton, IV ...... A61B 17/07207 606/130 |
| 2014/0005679 A1* | 1/2014 | Shelton, IV ...... A61B 17/07207 606/130 |
| 2014/0012131 A1 | 1/2014 | Heruth et al. |
| 2014/0031664 A1 | 1/2014 | Kang et al. |
| 2014/0046128 A1 | 2/2014 | Lee et al. |
| 2014/0046132 A1 | 2/2014 | Hoeg et al. |
| 2014/0046340 A1 | 2/2014 | Wilson et al. |
| 2014/0049629 A1* | 2/2014 | Siewerdsen ............ A61B 34/20 348/77 |
| 2014/0058406 A1 | 2/2014 | Tsekos |
| 2014/0066944 A1 | 3/2014 | Taylor et al. |
| 2014/0073914 A1 | 3/2014 | Lavallee et al. |
| 2014/0080086 A1 | 3/2014 | Chen |
| 2014/0081128 A1 | 3/2014 | Verard et al. |
| 2014/0088612 A1 | 3/2014 | Bartol et al. |
| 2014/0094694 A1 | 4/2014 | Moctezuma de la Barrera |
| 2014/0094851 A1 | 4/2014 | Gordon |
| 2014/0096369 A1 | 4/2014 | Matsumoto et al. |
| 2014/0100587 A1 | 4/2014 | Farritor et al. |
| 2014/0121676 A1 | 5/2014 | Kostrzewski et al. |
| 2014/0128882 A1 | 5/2014 | Kwak et al. |
| 2014/0135796 A1 | 5/2014 | Simon et al. |
| 2014/0142591 A1 | 5/2014 | Alvarez et al. |
| 2014/0142592 A1 | 5/2014 | Moon et al. |
| 2014/0148692 A1 | 5/2014 | Hartmann et al. |
| 2014/0163581 A1 | 6/2014 | Devengenzo et al. |
| 2014/0171781 A1 | 6/2014 | Stiles |
| 2014/0171900 A1 | 6/2014 | Stiles |
| 2014/0171965 A1 | 6/2014 | Loh et al. |
| 2014/0180308 A1 | 6/2014 | von Grunberg |
| 2014/0180309 A1 | 6/2014 | Seeber et al. |
| 2014/0187915 A1 | 7/2014 | Yaroshenko et al. |
| 2014/0188131 A1* | 7/2014 | Toth ........................ G16H 40/40 606/130 |
| 2014/0188132 A1 | 7/2014 | Kang |
| 2014/0194699 A1 | 7/2014 | Roh et al. |

(56) References Cited

U.S. PATENT DOCUMENTS

| | | | |
|---|---|---|---|
| 2014/0130810 A1 | 8/2014 | Azizian et al. | |
| 2014/0221819 A1 | 8/2014 | Sarment | |
| 2014/0222023 A1 | 8/2014 | Kim et al. | |
| 2014/0228631 A1 | 8/2014 | Kwak et al. | |
| 2014/0234804 A1 | 8/2014 | Huang et al. | |
| 2014/0257328 A1 | 9/2014 | Kim et al. | |
| 2014/0257329 A1 | 9/2014 | Jang et al. | |
| 2014/0257330 A1 | 9/2014 | Choi et al. | |
| 2014/0275760 A1 | 9/2014 | Lee et al. | |
| 2014/0275955 A1* | 9/2014 | Crawford | A61B 5/062 600/409 |
| 2014/0275985 A1 | 9/2014 | Walker et al. | |
| 2014/0276931 A1 | 9/2014 | Parihar et al. | |
| 2014/0276940 A1 | 9/2014 | Seo | |
| 2014/0276944 A1 | 9/2014 | Farritor et al. | |
| 2014/0276950 A1* | 9/2014 | Smaby | A61B 34/30 606/130 |
| 2014/0288413 A1 | 9/2014 | Hwang et al. | |
| 2014/0299648 A1 | 10/2014 | Shelton, IV et al. | |
| 2014/0303434 A1 | 10/2014 | Farritor et al. | |
| 2014/0303643 A1 | 10/2014 | Ha et al. | |
| 2014/0305995 A1 | 10/2014 | Shelton, IV et al. | |
| 2014/0309659 A1 | 10/2014 | Roh et al. | |
| 2014/0316436 A1 | 10/2014 | Bar et al. | |
| 2014/0323803 A1 | 10/2014 | Hoffman et al. | |
| 2014/0324070 A1 | 10/2014 | Min et al. | |
| 2014/0330288 A1 | 11/2014 | Date et al. | |
| 2014/0364720 A1 | 12/2014 | Darrow et al. | |
| 2014/0371577 A1 | 12/2014 | Maillet et al. | |
| 2014/0379130 A1 | 12/2014 | Lee et al. | |
| 2015/0039034 A1 | 2/2015 | Frankel et al. | |
| 2015/0085970 A1 | 3/2015 | Bouhnik et al. | |
| 2015/0146847 A1 | 5/2015 | Liu | |
| 2015/0150524 A1 | 6/2015 | Yorkston et al. | |
| 2015/0196261 A1 | 7/2015 | Funk | |
| 2015/0213633 A1 | 7/2015 | Chang et al. | |
| 2015/0335386 A1* | 11/2015 | Smith | A61B 5/06 606/130 |
| 2015/0335480 A1 | 11/2015 | Alvarez et al. | |
| 2015/0342647 A1 | 12/2015 | Frankel et al. | |
| 2016/0000513 A1* | 1/2016 | Shelton, IV | A61B 17/07207 606/130 |
| 2016/0005194 A1 | 1/2016 | Schretter et al. | |
| 2016/0106431 A1* | 4/2016 | Shelton, IV | A61B 17/07207 606/170 |
| 2016/0166329 A1 | 6/2016 | Langan et al. | |
| 2016/0206310 A1* | 7/2016 | Shelton, IV | A61B 17/07207 |
| 2016/0235480 A1 | 8/2016 | Scholl et al. | |
| 2016/0242849 A9* | 8/2016 | Crawford | A61B 17/025 |
| 2016/0242859 A1* | 8/2016 | Toth | G16H 40/40 |
| 2016/0249990 A1 | 9/2016 | Glozman et al. | |
| 2016/0302871 A1 | 10/2016 | Gregerson et al. | |
| 2016/0320322 A1 | 11/2016 | Suzuki | |
| 2016/0331335 A1 | 11/2016 | Gregerson et al. | |
| 2016/0331375 A1* | 11/2016 | Shelton, IV | A61B 17/07207 |
| 2017/0000485 A1* | 1/2017 | Shelton, IV | A61B 17/07207 |
| 2017/0027652 A1* | 2/2017 | Johnson | A61B 90/50 |
| 2017/0035519 A1* | 2/2017 | Smaby | A61B 34/30 |
| 2017/0042620 A1* | 2/2017 | Bartelme | A61B 34/20 |
| 2017/0071685 A1* | 3/2017 | Crawford | A61B 34/25 |
| 2017/0086831 A1* | 3/2017 | Shelton, IV | A61B 17/07207 |
| 2017/0135695 A1* | 5/2017 | Shelton, IV | A61B 17/07207 |
| 2017/0135770 A1 | 5/2017 | Scholl et al. | |
| 2017/0143284 A1 | 5/2017 | Sehnert et al. | |
| 2017/0143426 A1 | 5/2017 | Isaacs et al. | |
| 2017/0156816 A1 | 6/2017 | Ibrahim | |
| 2017/0181805 A1* | 6/2017 | Nixon | A61B 34/35 |
| 2017/0202629 A1 | 7/2017 | Maillet et al. | |
| 2017/0212723 A1 | 7/2017 | Atarot et al. | |
| 2017/0215825 A1 | 8/2017 | Johnson et al. | |
| 2017/0215826 A1 | 8/2017 | Johnson et al. | |
| 2017/0215827 A1 | 8/2017 | Johnson et al. | |
| 2017/0215881 A1* | 8/2017 | Shelton, IV | A61B 17/07207 |
| 2017/0231702 A1* | 8/2017 | Crawford | A61B 34/32 700/254 |
| 2017/0231710 A1 | 8/2017 | Scholl et al. | |
| 2017/0239002 A1* | 8/2017 | Crawford | A61B 34/30 |
| 2017/0239003 A1* | 8/2017 | Crawford | A61B 34/30 |
| 2017/0239006 A1* | 8/2017 | Crawford | A61B 34/32 |
| 2017/0239007 A1* | 8/2017 | Crawford | A61B 34/32 |
| 2017/0245944 A1* | 8/2017 | Crawford | A61B 34/76 |
| 2017/0245951 A1* | 8/2017 | Crawford | A61B 34/32 |
| 2017/0252112 A1* | 9/2017 | Crawford | A61B 17/025 |
| 2017/0252114 A1* | 9/2017 | Crawford | A61B 34/32 |
| 2017/0258426 A1 | 9/2017 | Risher-Kelly et al. | |
| 2017/0258533 A1* | 9/2017 | Crawford | A61B 17/025 |
| 2017/0258535 A1* | 9/2017 | Crawford | A61B 17/025 |
| 2017/0265949 A1* | 9/2017 | Crawford | A61B 17/025 |
| 2017/0273748 A1 | 9/2017 | Hourtash et al. | |
| 2017/0281145 A1* | 10/2017 | Crawford | A61B 17/025 |
| 2017/0290585 A1* | 10/2017 | Shelton, IV | A61B 17/07207 |
| 2017/0296277 A1 | 10/2017 | Hourtash et al. | |
| 2017/0304013 A1* | 10/2017 | Crawford | A61B 34/20 |
| 2017/0340397 A1* | 11/2017 | Smaby | A61B 90/361 |
| 2017/0348061 A1* | 12/2017 | Joshi | A61B 5/066 |
| 2017/0360493 A1 | 12/2017 | Zucher et al. | |
| 2017/0360517 A1* | 12/2017 | Crawford | A61B 34/20 |
| 2018/0000546 A1* | 1/2018 | Crawford | A61N 1/0529 |

FOREIGN PATENT DOCUMENTS

| | | |
|---|---|---|
| JP | 898843 A | 4/1996 |
| JP | 8313304 A | 11/1996 |
| WO | 02071369 A1 | 9/2002 |
| WO | 2012018816 A3 | 2/2012 |

OTHER PUBLICATIONS

Edward Rarnsden, Hat Effect Sensors; Theory and Application (2nd Edition), pp. 107-130, http://store.elsevier.com/Hall-Effect-Sensors/Edward-Ramsden/isbn-9780080523743/. Feb. 28, 2006.

Shuanghui, Hao et al., Study on a novel absolute magnetic encoder, Robotice and Biomemetics, 2009, ROBIO, 2009. IEEE, International Conference on IEEE. pp. 1773-1776, Feb. 22, 2009.

Eric M. Yeatmann et al., "Use of Scanned Detection in Optical Position Encoders", IEEE, Transactions of Instrumentation and Measurement. vol. 53, No. 1, pp. 37-44. http://www3.imperial.ac.uk/pls/portallive/docs/1/375913.PDF. Feb. 28, 2004.

* cited by examiner

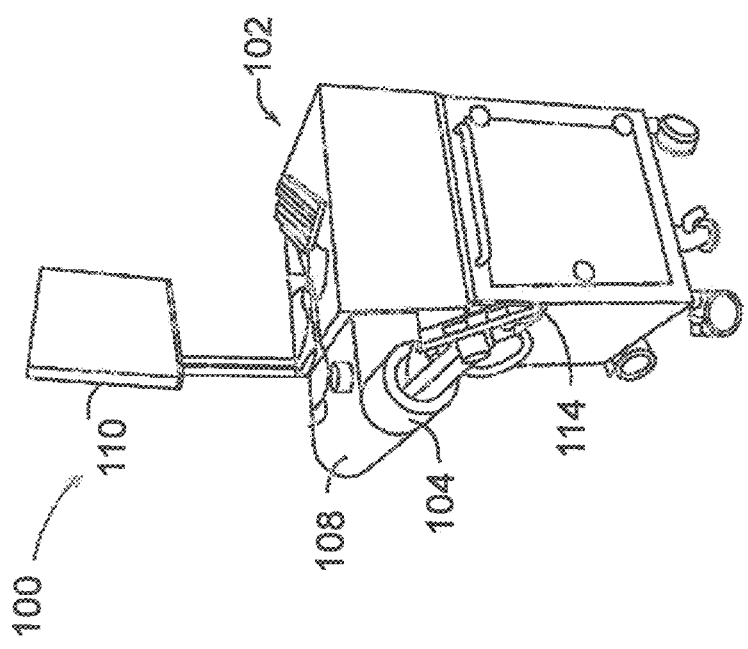

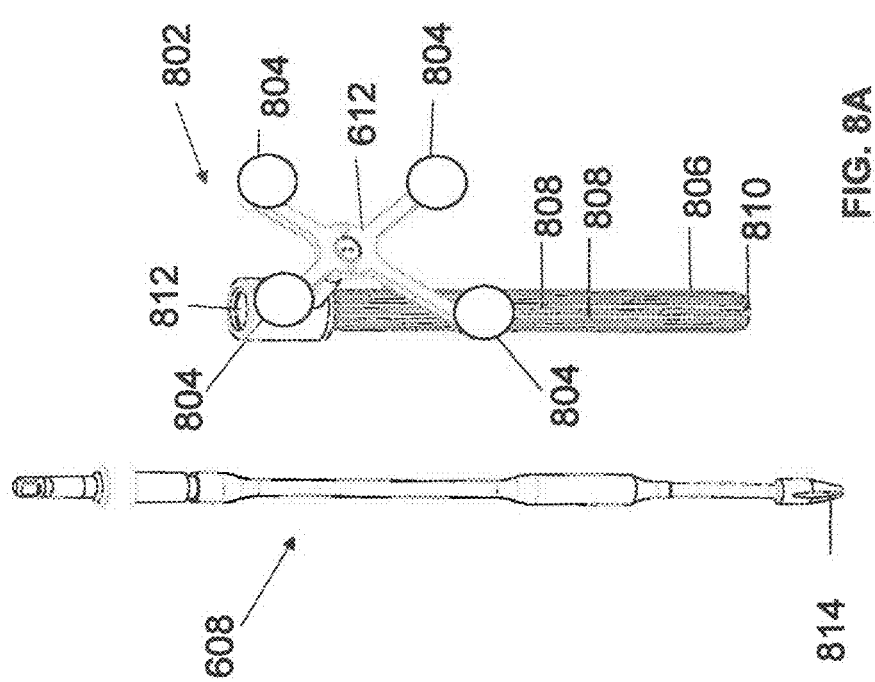

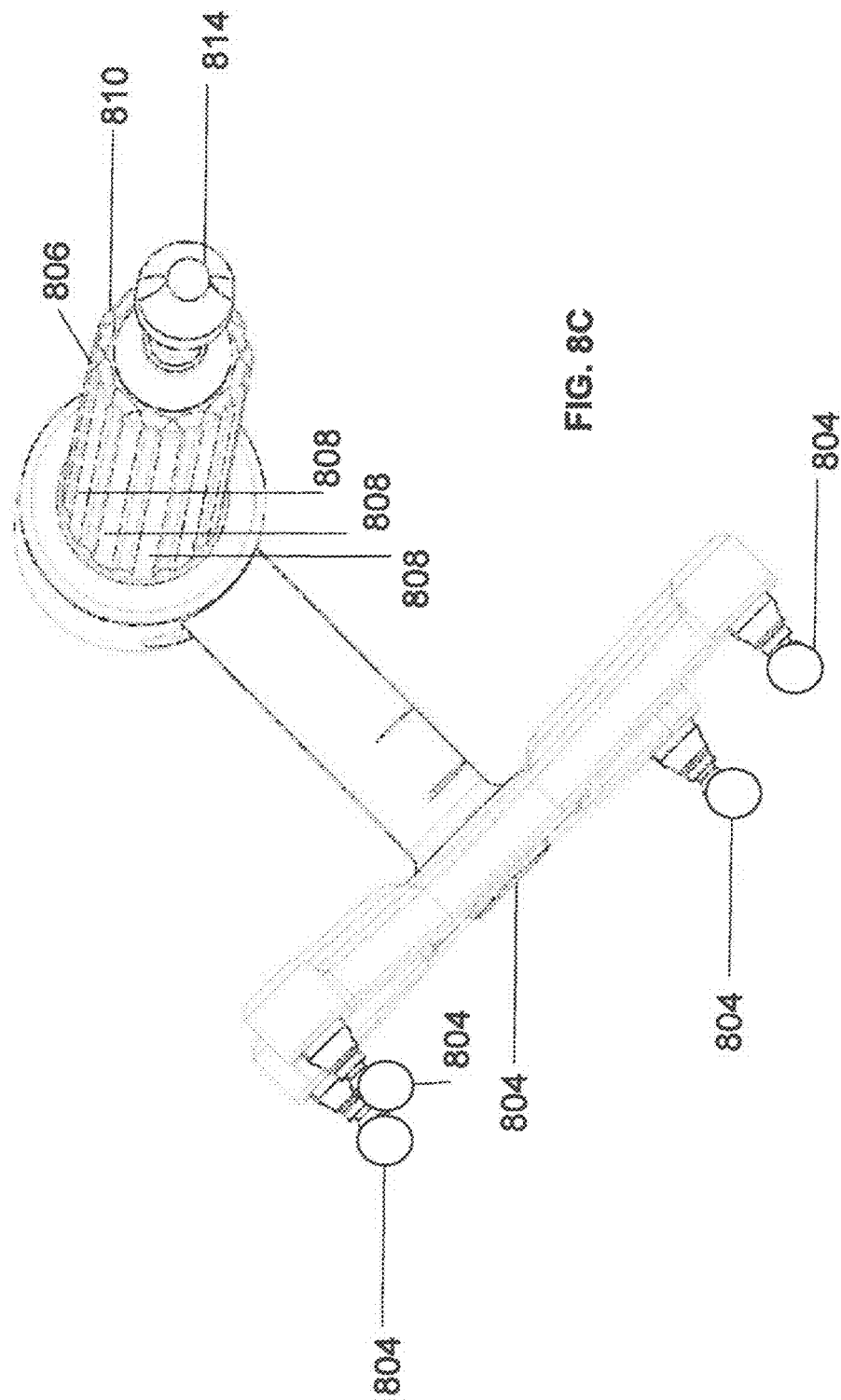

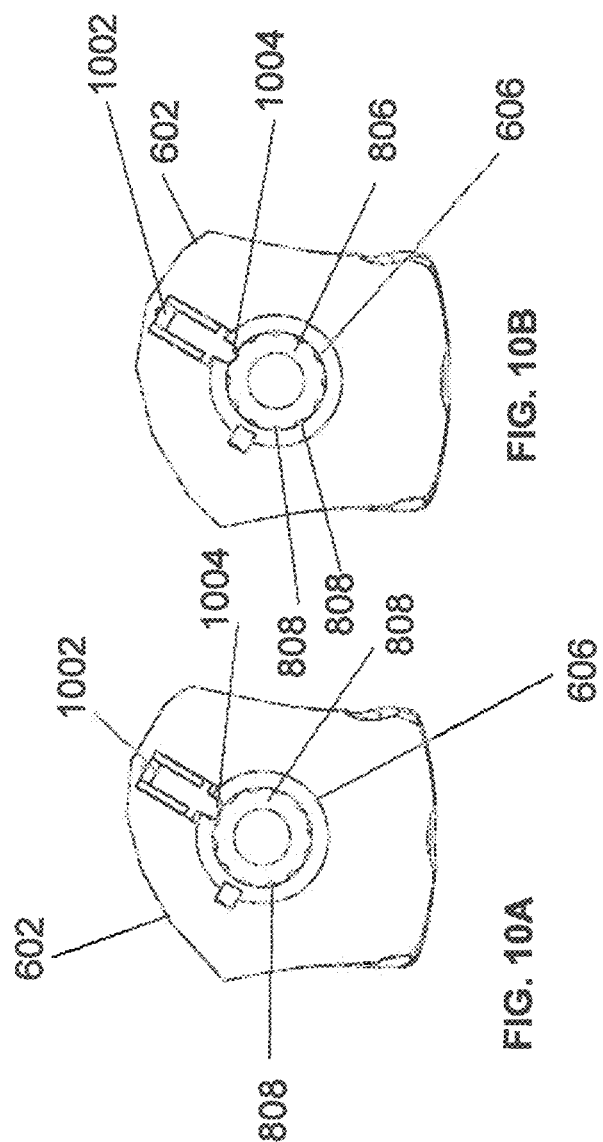

SURGICAL TOOL SYSTEMS AND METHODS

CROSS REFERENCE TO RELATED APPLICATIONS

This application is a continuation in part application of U.S. patent application Ser. No. 14/062,707 filed on Oct. 24, 2013 (published as U.S. Patent Publication No. 2014/0275955), which is a continuation in part application of U.S. patent application Ser. No. 13/924,505 filed on Jun. 21, 2013, which is a non-provisional patent application that claims priority to provisional application No. 61/662,702 filed on Jun. 21, 2012 and claims priority to provisional application No. 61/800,527 filed on Mar. 15, 2013, all of which are incorporated by reference in their entirety herein. In addition, this application is a continuation in part application of U.S. patent application Ser. No. 14/729,096 filed on Jun. 3, 2015 (published as U.S. Patent Publication No. 2015/0335386), which is a continuation application of U.S. patent application Ser. No. 13/542,560 filed on Jul. 5, 2012 (issued as U.S. Pat. No. 9,078,685), which is a continuation application of U.S. patent application Ser. No. 11/845,557 filed on Aug. 27, 2007 (issued as U.S. Pat. No. 8,219,178), which is a continuation in part application of U.S. patent application Ser. No. 11/838,027 filed on Aug. 13, 2007 (issued as U.S. Pat. No. 8,219,177), which is a continuation in part application of U.S. patent application Ser. No. 11/676,023 filed on Feb. 16, 2007 (issued as U.S. Pat. No. 8,010,181), which is a non-provisional patent application that claims priority to provisional application No. 60/775,816 filed on Feb. 16, 2006 and claims priority to provisional application No. 60/774,586 filed on Feb. 16, 2006, all of which are incorporated by reference in their entirety herein.

FIELD

The present disclosure generally relates to the use of robots in medical procedures and more particularly, the use of robots in surgical procedures that, for example, graphically depict anatomical structures of a patient on a display device and the location of surgical instruments in relation to those anatomical structures.

BACKGROUND

Various medical procedures require the accurate localization of a three-dimensional position of a surgical instrument within the body in order to effect optimized treatment. For example, some surgical procedures to fuse vertebrae require that a surgeon drill multiple holes into the bone structure at specific locations. To achieve high levels of mechanical integrity in the fusing system, and to balance the forces created in the bone structure, it is necessary that the holes are drilled at the correct location. Vertebrae, like most bone structures, have complex shapes including non-planar curved surfaces making accurate and perpendicular drilling difficult.

Conventionally, using currently-available systems and methods, a surgeon manually holds and positions a drill guide tube by using a guidance system to overlay the drill tube's position onto a three dimensional image of the anatomical structures of a patient, for example, bone structures of the patient. This manual process is both tedious, time consuming, and error-prone. Further, whether the surgery can be considered successful largely depends upon the dexterity of the surgeon who performs it. Thus, there is a need for the use of robot assisted surgery to more accurately position surgical instruments and more accurately depict the position of those instruments in relation to the anatomical structures of the patient.

Currently, limited robotic assistance for surgical procedures is available. For example, certain systems allow a user to control a robotic actuator. These systems convert a surgeon's gross movements into micro-movements of the robotic actuator to more accurately position and steady the surgical instruments when undergoing surgery. Although these systems may aid in eliminating hand tremor and provide the surgeon with improved ability to work through a small opening, like many of the robots commercially available today, these systems are expensive, obtrusive, and require a cumbersome setup for the robot in relation to the patient and the user (e.g., a surgeon). Further, for certain procedures, such as thoracolumbar pedicle screw insertion, these conventional methods are known to be error-prone and tedious.

The current systems have many drawbacks including but not limited to the fact that autonomous movement and precise placement of a surgical instrument can be hindered by a lack of mechanical feedback and/or a loss of visual placement once the instrument is submerged within a portion of a patient. These drawbacks make the existing surgical applications error prone resulting in safety hazards to the patient as well as the surgeon during surgical procedures.

In addition, current robot assisted systems suffer from other disadvantages. The path and angle in which a surgical instrument is inserted into a patient (a trajectory of the instrument) may be limited due to the configuration of the robot arm and the manner in which it can move. For example, some current systems may not have enough range of motion or movement to place the surgical instrument at a trajectory ideal for placement into the patient and/or at a position that allows the surgeon an optimal view for performing the surgery.

The present disclosure overcomes the disadvantages of current robot assisted surgical applications. For example, the present disclosure allows for precisely locating anatomical structures in open, percutaneous, or minimally invasive surgery (MIS) procedures and positioning surgical instruments or implants during surgery. In addition, the present disclosure may improve stereotactic surgical procedures by allowing for identification and reference to a rigid anatomical structure relative to a pre-op computerized tomography (CT) scan, intra-op CT scan or fluoroscopy/x-ray based image of the anatomy. Further, the present disclosure may integrate a surgical robotic arm, a local positioning system, a dynamic reference base, and planning software to assist a surgeon in performing medical procedures in a more accurate and safe manner thereby reducing the error prone characteristics of current robot assisted systems and methods.

SUMMARY

Exemplary embodiments of the present disclosure may provide a surgical robot system comprising a robot base having a display, a robot arm coupled to the robot base, wherein movement of the robot arm is electronically controlled by the robot base, and an end-effector, coupled to the robot arm, containing one or more end-effector tracking markers. The robot base may be in electronic communication with the one or more end-effector tracking markers and the display is configured to indicate a location of the end-effector in relation to at least one of the robot base and the robot arm.

Exemplary embodiments of the present disclosure may also provide a surgical robot system comprising a robot base having a display, a robot arm coupled to the robot base, wherein movement of the robot arm is electronically controlled by the robot base, and an end-effector, coupled to the robot arm, containing an instrument detecting sensor. The guide tube, disposed in the end-effector, may be configured to receive an instrument assembly housing an instrument, and the instrument detecting sensor may be configured to determine the presence of the instrument when the instrument assembly enters the guide tube.

Exemplary embodiments of the present disclosure may provide a surgical robot system comprising a surgical robot base, a surgical robot arm electronically coupled to the surgical robot base, and an end-effector, coupled to the surgical robot arm, having a guide tube configured to receive an instrument assembly, the instrument assembly containing one or more grooves disposed along a length of the instrument assembly. The guide tube may be configured to engage at least one of the grooves to restrict rotational movement of the instrument assembly within the guide tube.

Exemplary embodiments of the present disclosure may provide a surgical robot system comprising a robot base, a robot arm electronically coupled to the robot base, wherein the robot arm contains at least one depression and a magnet disposed proximate to each of the at least one depression, a clamp containing one or more balls, each of the one or more balls configured to magnetically engage one of the at least one depression, and an end-effector, electronically coupled to the robot base, configured to be coupled to the clamp.

Exemplary embodiments of the present disclosure may provide a surgical robot system comprising a robot base, a robot arm electronically coupled to the robot base, and an end-effector electronically coupled to the robot base. The robot arm may contain a primary coil and the end-effector may contain a secondary coil wherein power is transmitted from the primary coil to the secondary coil to wirelessly power the end-effector.

Exemplary embodiments of the present disclosure may provide a surgical robot system comprising a dynamic reference base (DRB) attached to patient fixture instrument, wherein the dynamic reference base has one or more DRB markers indicating a position of the patient fixture instrument in a navigational space, and a registration fixture, having one or more registration markers, indicating a location of a target anatomical structure in the navigational space and one or more registration fiducials indicating a location of the target anatomical structure in an image space. The surgical robot system may be configured to associate the location of the target anatomical structure with the patient fixture instrument in the navigational space and the image space taking into account a relationship between the one or more registration markers and the one or more fiducials and the relationship between the registration makers and the DRB markers. The patient fixture instrument is located in a position different from the target anatomical structure.

DESCRIPTION OF THE DRAWINGS

FIGS. 1A-1B illustrate a surgical robot in accordance with an exemplary embodiment.

FIGS. 8A-C illustrate an instrument and an instrument assembly in accordance with an exemplary embodiment.

FIG. 10A-B illustrate an end-effector and instrument assembly in accordance with an exemplary embodiment.

DETAILED DESCRIPTION

Figure 1B:
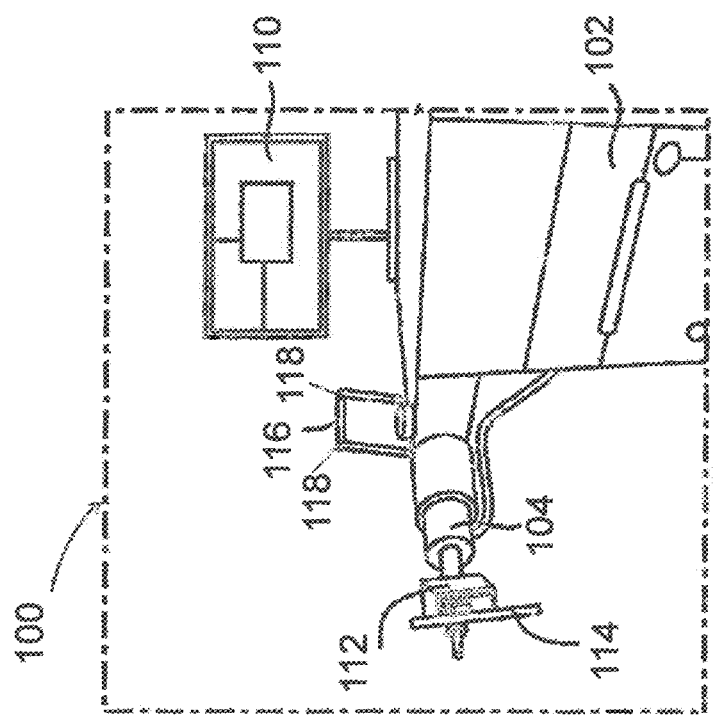

It is to be understood that the present disclosure is not limited in its application to the details of construction and the arrangement of components set forth in the description herein or illustrated in the drawings. The teachings of the present disclosure may be used and practiced in other embodiments and practiced or carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items. Unless specified or limited otherwise, the terms "mounted," "connected," "supported," and "coupled" and variations thereof are used broadly and encompass both direct and indirect mountings, connections, supports, and couplings. Further, "connected" and "coupled" are not restricted to physical or mechanical connections or couplings.

The following discussion is presented to enable a person skilled in the art to make and use embodiments of the present disclosure. Various modifications to the illustrated embodiments will be readily apparent to those skilled in the art, and the principles herein can be applied to other embodiments and applications without departing from embodiments of the present disclosure. Thus, the embodiments are not intended to be limited to embodiments shown, but are to be accorded the widest scope consistent with the principles and features disclosed herein. The following detailed description is to be read with reference to the figures, in which like elements in different figures have like reference numerals. The figures, which are not necessarily to scale, depict selected embodiments and are not intended to limit the scope of the embodiments. Skilled artisans will recognize the examples provided herein have many useful alternatives and fall within the scope of the embodiments.

Figure 1C:
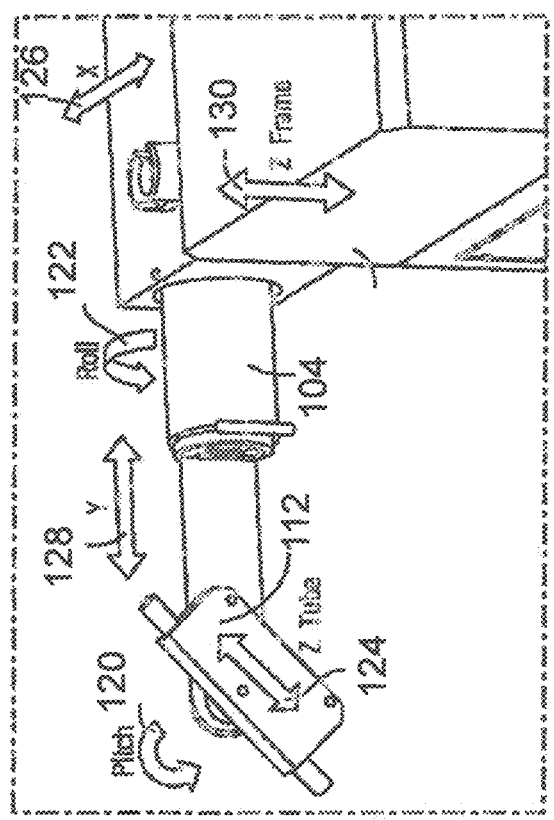
FIG. 1C illustrates a portion of a surgical robot with control of the translation and orientation of the end-effector in accordance with an exemplary embodiment.
Figure 1D:
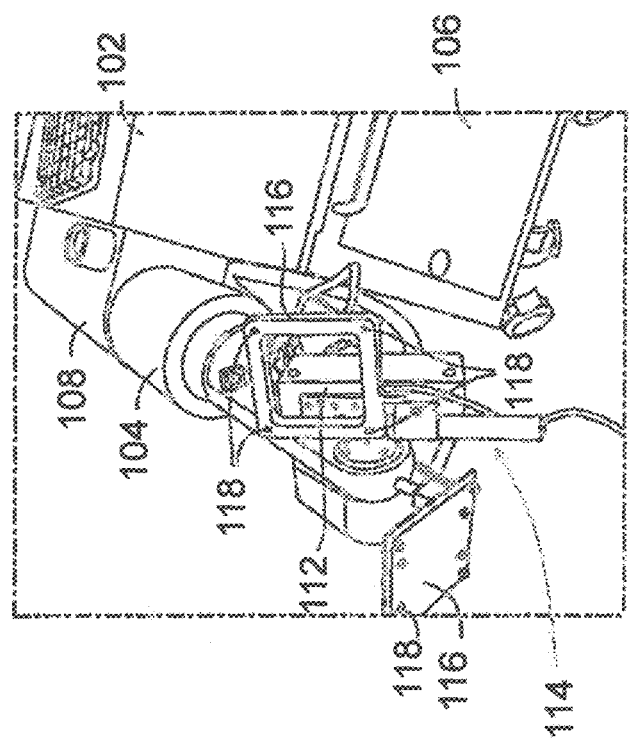
FIG. 1D illustrates a partial view of a surgical robot having a plurality of optical markers mounted for calibration and tracking movement in accordance with an exemplary embodiment.

FIGS. 1A, 1B, and 1D illustrate a surgical robot system 100 in accordance with an exemplary embodiment. Surgical robot system 100 may include a surgical robot 102, a robot arm 104, a base 106, a housing 108, a display 110, an end-effector or end-effectuator 112, a guide tube 114, a tracking array 116, and tracking markers 118.

FIG. 1C illustrates a portion of a surgical robot system 100 with control of the translation and orientation of end-effector 112 in accordance with an exemplary embodiment.

As shown in FIGS. 1A and 1B, surgical robot 102 can comprise a display 110 and a housing 108. Display 110 can be attached to the surgical robot 102 and in other exemplary embodiments, display 110 can be detached from surgical robot 102, either within a surgical room with the surgical robot 102, or in a remote location. In some embodiments, housing 108 can comprise robot arm 104 and an end-effector 112. End-effector 112 may be coupled to the robot arm 104 and controlled by at least one motor. In exemplary embodiments, end-effector 112 can comprise a surgical instrument used to perform surgery on a patient 210. In exemplary embodiments, end-effector 112 can be coupled to the surgical instrument. As used herein, the term "end-effector" is used interchangeably with the term "effectuator element." In some embodiments, end-effector 112 can comprise any known structure for effecting the movement of the surgical instrument in a desired manner.

FIG. 1C illustrates a portion of a surgical robot 102 with control of the translation and orientation of end-effector 112 in accordance with an exemplary embodiment. As shown, some embodiments include a surgical robot system 100 capable of using robot 102 with an ability to move end-effector 112 along x-, y-, and z-axes (see 126, 128, 130 in FIG. 1C). In this embodiment, x-axis 126 can be orthogonal to y-axis 128 and z-axis 130, y-axis 128 can be orthogonal to x-axis 126 and z-axis 130, and z-axis 130 can be orthogonal to x-axis 126 and y-axis 128. In an exemplary embodiment, robot 102 can be configured to effect movement of end-effector 112 along one axis independently of the other axes. For example, in some exemplary embodiments, robot 102 can cause the end-effector 112 to move a given distance of 500 mm or more along x-axis 126 without causing any substantial movement of end-effector 112 along y-axis 128 or z-axis 130. As used in this context "substantial" may mean a deviation of more than two degrees or 2 mm from an intended path or some other predetermined deviation that may be appropriate for the surgical application.

In some further exemplary embodiments, end-effector 112 can be configured for selective rotation about one or more of x-axis 126, y-axis 128, and a Z Frame axis 130 (such that one or more of the Euler Angles (e.g., roll, pitch, and/or yaw) associated with end-effector 112 can be selectively controlled). For example, roll 122 is selective rotation about y-axis 128 without substantial deviation about or along x-axis 126 or Z Frame axis 130; pitch 120 is selective rotation about x-axis 126 without substantial deviation about or along y-axis 128 or Z Frame axis 130. In some exemplary embodiments, during operation, end-effector 112 and/or the surgical instrument may be aligned with a selected orientation axis (labeled "Z Tube" 64 in FIG. 1C) that can be selectively varied and monitored by robot system 100. End-effector 112 may contain a linear actuator that causes guide tube 114 to move in Z Tube axis 64 direction.

Figure 2:
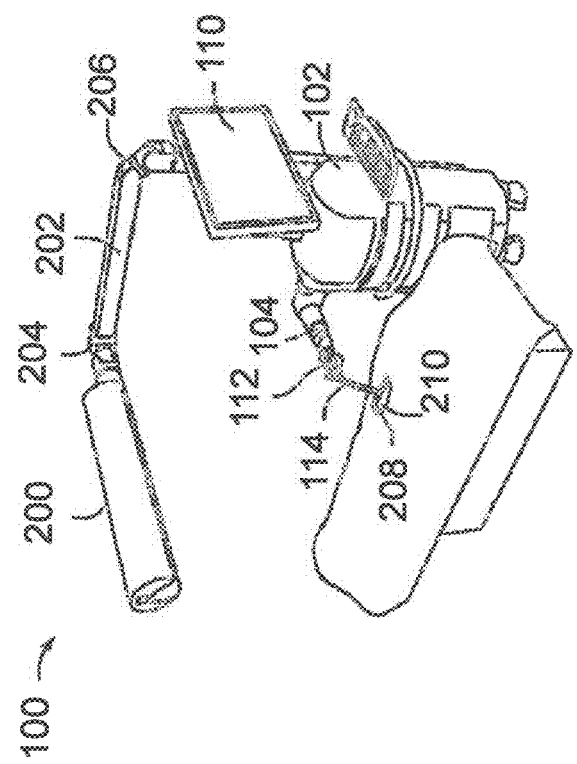
FIG. 2 illustrates a surgical robot operating on a patient in accordance with an exemplary embodiment.

In some exemplary embodiments, selective control of the translation and orientation of end-effector 112 can permit performance of medical procedures with significantly improved accuracy compared to conventional robots that utilize, for example, a six degree of freedom robot arm comprising only rotational axes. For example, in some exemplary embodiments, as shown in FIG. 2, surgical robot system 100 may be used to operate on patient 210, and robot arm 104 that can be positioned above the body of patient 210, with end-effector 112 selectively angled relative to the z-axis toward the body of patient 210.

In some exemplary embodiments, the position of the surgical instrument can be dynamically updated so that surgical robot 102 can be aware of the location of the surgical instrument at all times during the procedure. Consequently, in some exemplary embodiments, surgical robot 102 can move the surgical instrument to the desired position quickly, with minimal damage to patient 210, and without any further assistance from a physician (unless the physician so desires). In some further embodiments, surgical robot 102 can be configured to correct the path of the surgical instrument if the surgical instrument strays from the selected, preplanned trajectory. In some exemplary embodiments, surgical robot 102 can be configured to permit stoppage, modification, and/or manual control of the movement of end-effector 112 and/or the surgical instrument. Thus, in use, in exemplary embodiments, a physician or other user can operate the system 100, and has the option to stop, modify, or manually control the autonomous movement of end-effector 112 and/or the surgical instrument. Further details of surgical robot system 100 including the control and movement of a surgical instrument by surgical robot 102 can be found in co-pending U.S. patent application Ser. No. 13/924,505 from which this application claims priority under 35 U.S.C. § 120, and which is incorporated herein by reference in its entirety.

As shown in FIGS. 1B and 1D, in exemplary embodiments, robotic surgical system 100 can comprise a plurality of tracking markers 118 configured to track the movement of robot arm 104, end-effector 112, and/or the surgical instrument in three dimensions. It should be appreciated that three dimensional positional information from tracking markers 118 can be used in conjunction with the one dimensional linear or rotational positional information from absolute or relative conventional linear or rotational encoders on each axis of robot 102 to maintain a high degree of accuracy. In exemplary embodiments, the plurality of tracking markers 118 can be mounted (or otherwise secured) thereon an outer surface of the robot 102, such as, for example and without limitation, on base 106 of robot 102, or robot arm 104 (see for example FIG. 1B). Further, in exemplary embodiments, the plurality of tracking markers 118 can be positioned on base 106 of robot 102 spaced from surgical field 208 to reduce the likelihood of being obscured by the surgeon, surgical tools, or other parts of robot 102. In exemplary embodiments, at least one tracking marker 118 of the plurality of tracking markers 118 can be mounted or otherwise secured to end-effector 112 (see for example FIG. 1D).

In exemplary embodiments, system 100 can use tracking information collected relative to the robot base 106 to calculate the orientation and coordinates of the surgical instrument held in the tube 114 based on encoder counts along x-axis 126, y-axis 128, z-axis 130, Z-tube axis 124, and the roll 122 and pitch 120 axes.

In exemplary embodiments, one or more of markers 118 may be optical markers and at least one optical marker may be positioned on the robot 102 between the base 106 of the robot 102 and end-effector 112 instead of, or in addition to, other markers 118 on base 106. In some embodiments, the positioning of one or more tracking markers 118 on end-effector 112 can maximize the accuracy of the positional measurements by serving to check or verify the position of end-effector 112 (calculated from the positional information of markers 118 on base 106 and encoder counts of z-axis 130, x-axis 126, y-axis 128, roll axis 122, pitch axis 120, and Z-tube axis 124).

In exemplary embodiments, the at least one tracking marker 118 can be mounted to a portion of the robot 102 that effects movement of end-effector 112 and/or the surgical instrument along the x-axis to enable the at least one tracking marker 118 to move along x-axis 126 as end-effector 112 and the surgical instrument move along the x-axis 126 (see FIG. 1D). In exemplary embodiments, placement of tracking markers 118 as described can reduce the likelihood of a surgeon blocking one or more tracking markers 118 from the cameras or detection device, or one or more tracking markers 118 becoming an obstruction to surgery.

In exemplary embodiments, because of the high accuracy in calculating the orientation and position of end-effector 112 based on an output of one or more tracking markers 118 and/or encoder counts from each axis, it can be possible to very accurately determine the position of end-effector 112. For example, in exemplary embodiments, without requiring knowledge of the counts of axis encoders for the z-axis 130 (which is between the x-axis 126 and the base 106), knowing only the position of markers 118 on the x-axis 126 and the counts of encoders on the y-axis 128, roll axis 62, pitch axis 120, and Z-tube axis 124 can enable computation of the position of end-effector 112. In some embodiments, the placement of markers 118 on any intermediate axis of robot 102 can permit the exact position of end-effector 112 to be calculated based on location of such markers 118 and counts of encoders on axes (126, 120, 122, and 124) between markers 118 and end-effector 112. Further details of surgical robot system 100 including the control, movement and tracking of surgical robot 102 and of a surgical instrument can be found in co-pending U.S. patent application Ser. No. 13/924,505 from which this application claims priority under 35 U.S.C. § 120, and which is incorporated herein by reference in its entirety as earlier recited.

Exemplary embodiments include one or more markers coupled to the surgical instrument as described in greater detail below. In exemplary embodiments, these markers as well as markers 118 can comprise conventional infrared light-emitting diodes or an Optotrak® diode capable of being tracked using a commercially available infrared optical tracking system such as Optotrak®. Optotrak® is a registered trademark of Northern Digital Inc., Waterloo, Ontario, Canada. In other embodiments, markers 118 can comprise conventional reflective spheres capable of being tracked using a commercially available optical tracking system such as Polaris Spectra. Polaris Spectra is also a registered trademark of Northern Digital, Inc.

Referring to FIG. 2, surgical robot system 100 is shown and further includes cameras 200, a camera arm 202, camera arm joints 204 and 206. FIG. 2 further depicts surgical field 208 and patient 210.

In exemplary embodiments, light emitted from and/or reflected by markers 118 and markers on the surgical instrument can be read by camera 200 and can be used to monitor the location and movement of robot 102 (see for example camera 200 mounted on the camera arm 202 and capable of movement through camera arm joint 204 and camera arm joint 206 shown in FIG. 2). In exemplary embodiments, markers 118 and the markers on the surgical instrument can comprise a radio-frequency and/or electromagnetic reflector or transceiver and the camera 200 can include or be replaced by a radio-frequency and/or electromagnetic transceiver.

Figure 3:
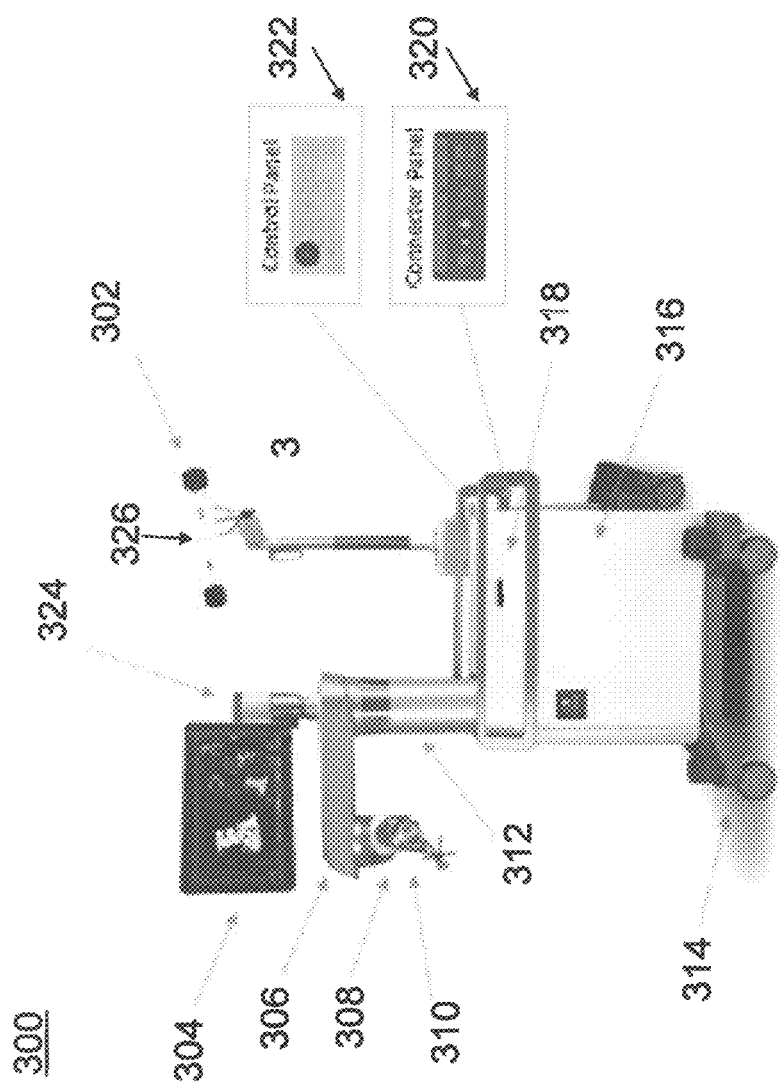
FIG. 3 illustrates a surgical robot in accordance with an exemplary embodiment.

FIG. 3 illustrates a surgical robot system 300 and camera stand 302 consistent with an exemplary embodiment of the present disclosure. Surgical robot system 300 may comprise display 304, upper arm 306, lower arm 308, end-effector 310, vertical column 312, casters 314, cabinet 316, tablet drawer 318, connector panel 320, control panel 322, and ring 324. Camera stand 302 may comprise camera 326. These components are described in greater with respect to FIG. 5.

Figure 4:
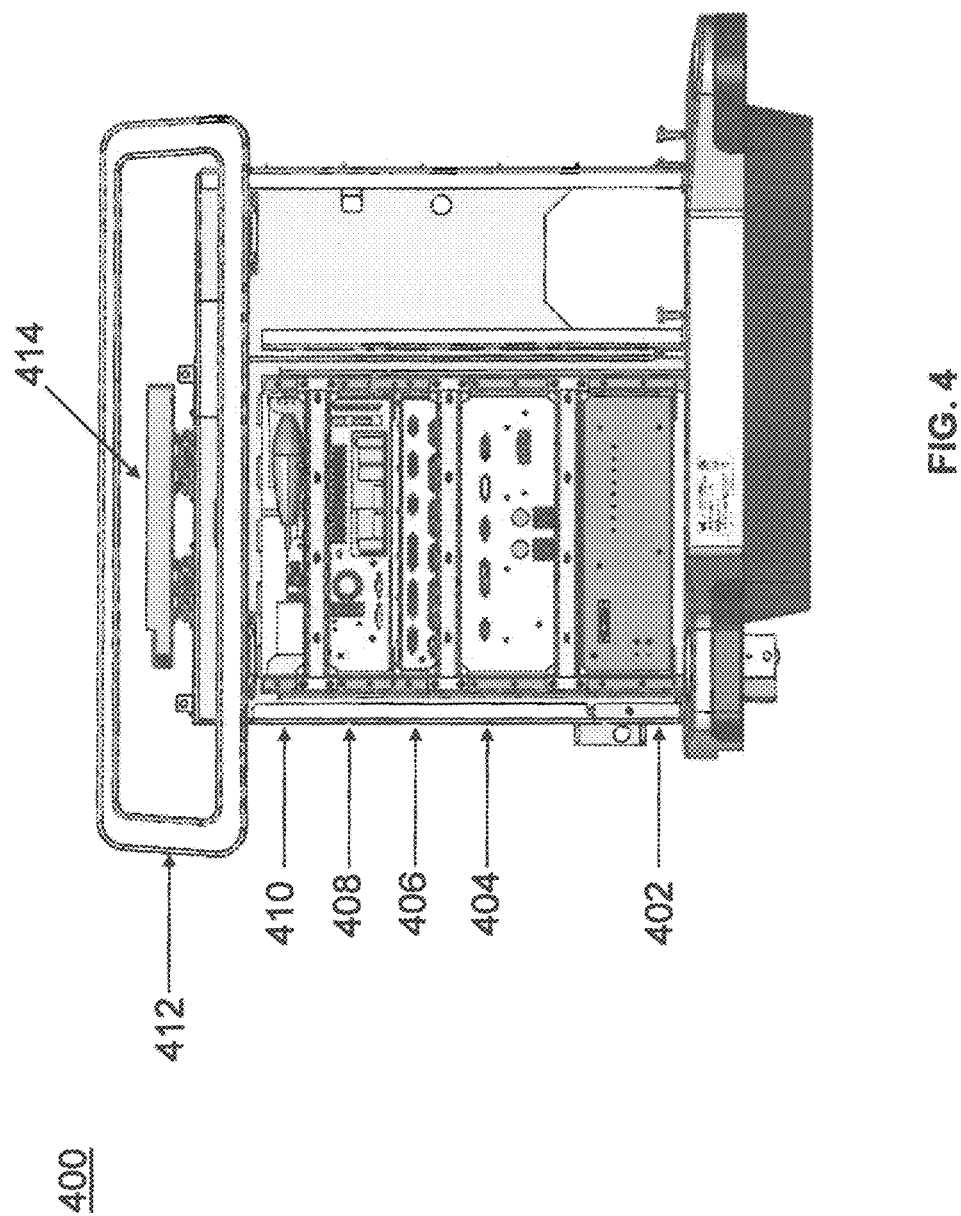
FIG. 4 illustrates a portion of a surgical robot in accordance with an exemplary embodiment.

FIG. 4 illustrates a base 400 consistent with an exemplary embodiment of the present disclosure. Base 400 may be a portion of surgical robot system 300 and comprise cabinet 316. Cabinet 316 may house certain components of surgical robot system 300 including but not limited to a battery 402, a power distribution module 404, a platform interface board module 406, a computer 408, a handle 412, and a tablet drawer 414. The connections and relationship between these components is described in greater detail with respect to FIG. 5.

Figure 5:
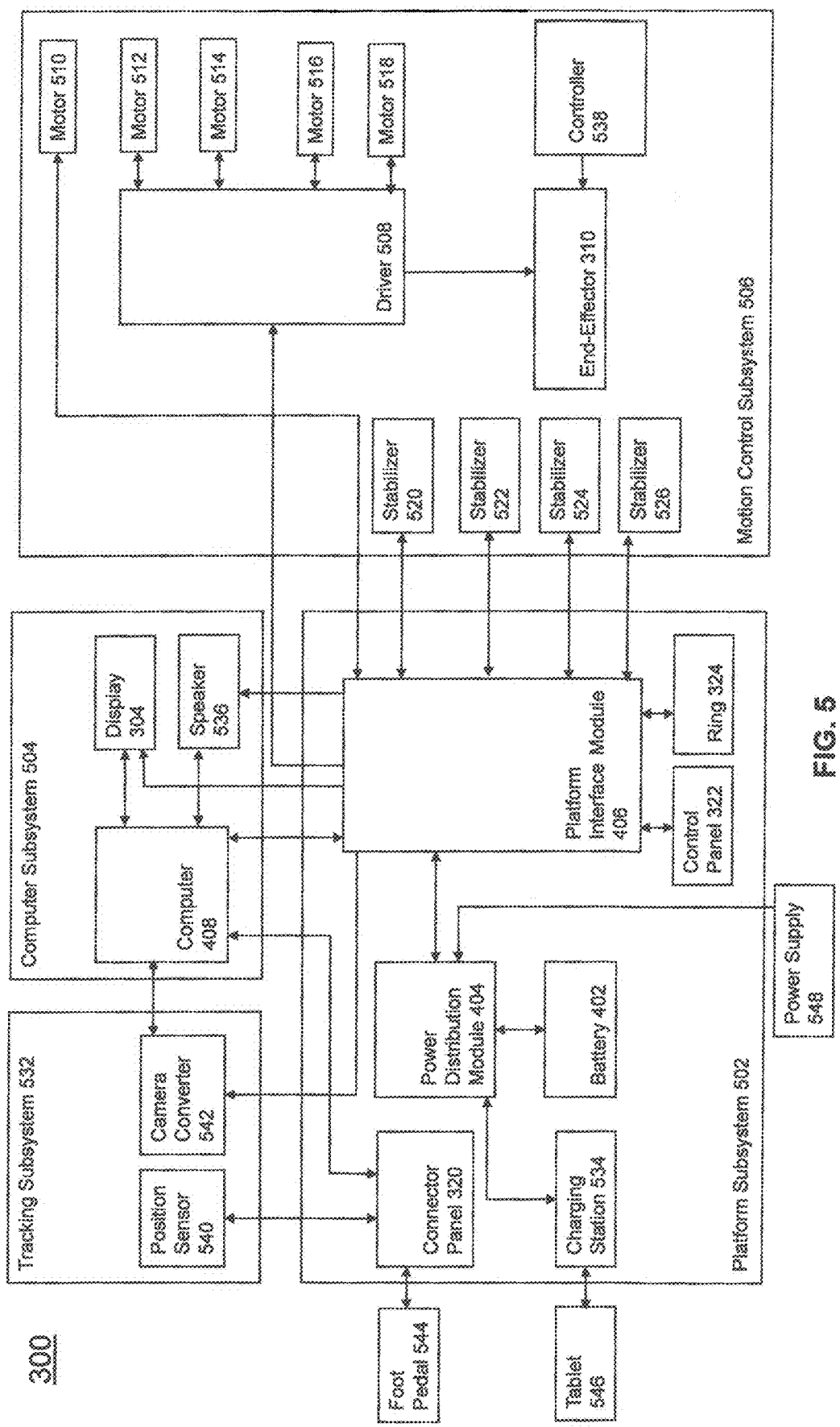
FIG. 5 illustrates a block diagram of a surgical robot in accordance with an exemplary embodiment.

FIG. 5 illustrates a block diagram of certain components of an exemplary embodiment of surgical robot system 300. Surgical robot system 300 may comprise platform subsystem 502, computer subsystem 504, motion control subsystem 506, and tracking subsystem 532. Platform subsystem 502 may further comprise battery 402, power distribution module 404, platform interface board module 406, and tablet charging station 534. Computer subsystem 504 may further comprise computer 408, display 304, and speaker 536. Motion control subsystem 506 may further comprise driver circuit 508, motors 510, 512, 514, 516, 518, stabilizers 520, 522, 524, 526, end-effector 310, and controller 538. Tracking subsystem 532 may further comprise position sensor 540 and camera converter 542. System 300 may also comprise a foot pedal 544 and tablet 546.

Input power is suppled to system 300 via a power source 548 which may be provided to power distribution module 404. Power distribution module 404 receives input power and is configured to generate different power supply voltages that are provided to other modules, components, and subsystems of system 300. Power distribution module 404 may be configured to provide different voltage supplies to platform interface module 406, which may be provided to other components such as computer 408, display 304, speaker 536, driver 508 to, for example, power motors 512, 514, 516, 518 and end-effector 310, motor 510, ring 324, camera converter 542, and other components for system 300 for example, fans for cooling the electrical components within cabinet 316.

Power distribution module 404 may also provide power to other components such as tablet charging station 534 that may be located within tablet drawer 318. Tablet charging station 534 may be in wireless or wired communication with tablet 546 for charging table 546. Tablet 546 may be used by a surgeon consistent with the present disclosure and described herein.

Power distribution module 404 may also be connected to battery 402, which serves as temporary power source in the event that power distribution module 404 does not receive power from input power 548. At other times, power distribution module 404 may serve to charge battery 402 if necessary.

Other components of platform subsystem 502 may also include connector panel 320, control panel 322, and ring 324. Connector panel 320 may serve to connect different devices and components to system 300 and/or associated components and modules. Connector panel 320 may contain one or more ports that receive lines or connections from different components. For example, connector panel 320 may have a ground terminal port that may ground system 300 to other equipment, a port to connect foot pedal 544 to system 300, a port to connect to tracking subsystem 532, which may comprise position sensor 540, camera converter 542, and cameras 326 associated with camera stand 302. Connector panel 320 may also include other ports to allow USB, Ethernet, HDMI communications to other components, such as computer 408.

Control panel 322 may provide various buttons or indicators that control operation of system 300 and/or provide information regarding system 300. For example, control panel 322 may include buttons to power on or off system 300, lift or lower vertical column 312, and lift or lower stabilizers 520-526 that may be designed to engage casters 314 to lock system 300 from physically moving. Other buttons may stop system 300 in the event of an emergency, which may remove all motor power and apply mechanical brakes to stop all motion from occurring. Control panel 322 may also have indicators notifying the user of certain system conditions such as a line power indicator or status of charge for battery 402.

Ring 324 may be a visual indicator to notify the user of system 300 of different modes that system 300 is operating under and certain warnings to the user.

Computer subsystem 504 includes computer 408, display 304, and speaker 536. Computer 504 includes an operating system and software to operate system 300. Computer 504 may receive and process information from other components (for example, tracking subsystem 532, platform subsystem 502, and/or motion control subsystem 506) in order to display information to the user. Further, computer subsystem 504 may also include speaker 536 to provide audio to the user.

Tracking subsystem 532 may include position sensor 504 and converter 542. Tracking subsystem 532 may correspond to camera stand 302 including camera 326 as described with respect to FIG. 3. Position sensor 504 may be camera 326. Tracking subsystem may track the location of certain markers that are located on the different components of system 300 and/or instruments used by a user during a surgical procedure. This tracking may be conducted in a manner consistent with the present disclosure including the use of infrared technology that tracks the location of active or passive elements, such as LEDs or reflective markers, respectively. The location, orientation, and position of structures having these types of markers may be provided to computer 408 which may be shown to a user on display 304. For example, a surgical instrument having these types of markers and tracked in this manner (which may be referred to as a navigational space) may be shown to a user in relation to a three dimensional image of a patient's anatomical structure.

Motion control subsystem 506 may be configured to physically move vertical column 312, upper arm 306, lower arm 308, or rotate end-effector 310. The physical movement may be conducted through the use of one or more motors 510-518. For example, motor 510 may be configured to vertically lift or lower vertical column 312. Motor 512 may be configured to laterally move upper arm 308 around a point of engagement with vertical column 312 as shown in FIG. 3. Motor 514 may be configured to laterally move lower arm 308 around a point of engagement with upper arm 308 as shown in FIG. 3. Motors 516 and 518 may be configured to move end-effector 310 in a manner such that one may control the roll and one may control the tilt, thereby providing multiple angles that end-effector 310 may be moved. These movements may be achieved by controller 538 which may control these movements through load cells disposed on end-effector 310 and activated by a user engaging these load cells to move system 300 in a desired manner.

Moreover, system 300 may provide for automatic movement of vertical column 312, upper arm 306, and lower arm 308 through a user indicating on display 304 (which may be a touchscreen input device) the location of a surgical instrument or component on three dimensional image of the patient's anatomy on display 304. The user may initiate this automatic movement by stepping on foot pedal 544 or some other input means.

Figure 6:
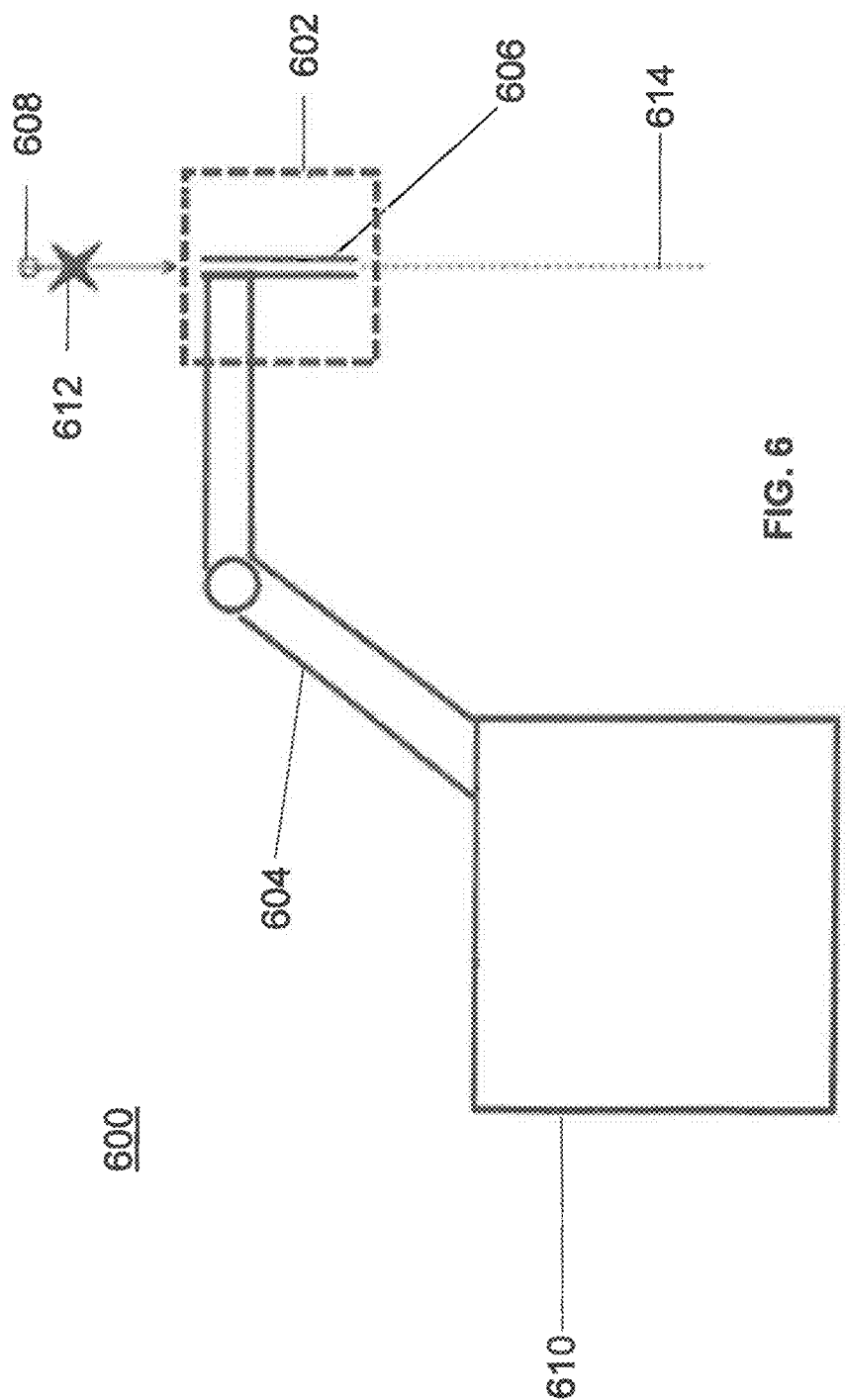
FIG. 6 illustrates a surgical robot in accordance with an exemplary embodiment.

FIG. 6 illustrates a surgical robot system 600 consistent with an exemplary embodiment. Surgical robot system 600 may comprise end-effector 602, robot arm 604, guide tube 606, instrument 608, and robot base 610. Instrument tool 608 may be attached to a tracking array 612 and have an associated trajectory 614. Trajectory 614 may represent a path of movement that instrument tool 608 is configured to travel once it is secured in guide tube 606, for example, a path of insertion of instrument tool 608 into a patient. In an exemplary operation, robot base 610 may be configured to be in electronic communication with robot arm 604 and end-effector 602 so that surgical robot system 600 may assist a user (for example, a surgeon) in operating on a patient. Surgical robot system 600 may be consistent with previously described surgical robot system 100 and 300.

A tracking array 612 may be mounted on instrument 608 to monitor the location and orientation of instrument tool 608. As described in greater detail below with respect to FIG. 8A, tracking array 612 may be attached to an instrument assembly 802 and may comprise markers 804. Instrument assembly 802 may house instrument 608 as described in further detail below with respect to FIG. 8B. Markers 804 may be, for example, light emitting diodes and/or other types of markers as described consistent with the present disclosure. The tracking devices may be one or more line of sight devices associated with the surgical robot system. As an example, the tracking devices may be cameras associated with the surgical robot system and may also track tracking array 612 for a defined domain or relative orientations of the instrument in relation to the robot arm, the robot base, and/or a patient. The tracking devices may be consistent with those structures described in connection with camera stand 302 and tracking subsystem 532.

Figure 7C:
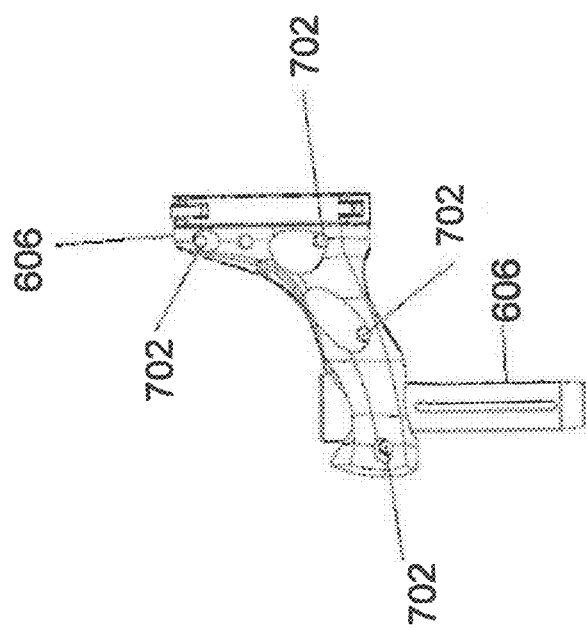
FIGS. 7A-C illustrate an end-effector in accordance with an exemplary embodiment.
Figure 7A:
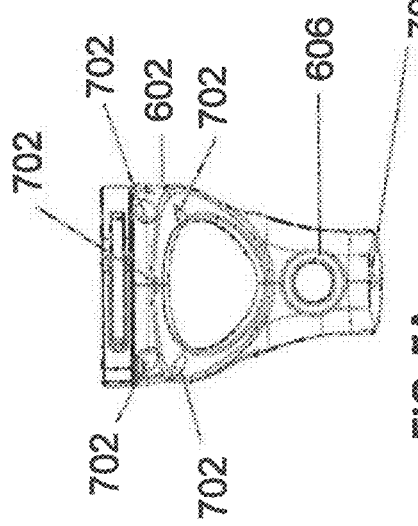
Figure 7B:
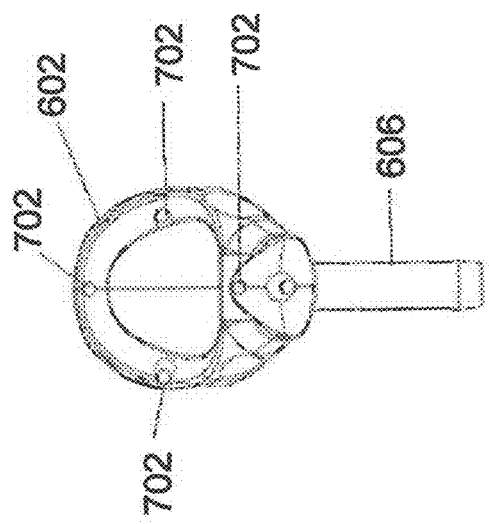

FIGS. 7A, 7B, and 7C illustrate a top view, front view, and side view, respectively, of end-effector 602 consistent with an exemplary embodiment. End-effector 602 may additionally comprise one or more markers 702. Markers 702 may be light emitting diodes or other types of markers that have been previously described.

Markers 702 may be disposed on end-effector 602 in a manner such that the markers are visible by one or more tracking devices associated with the surgical robot system. The tracking devices may track end-effector 602 as it moves to different positions and viewing angles by following the movement of tracking markers 702. The location of markers 702 and/or end-effector 602 may be shown on a display associated with the surgical robot system, for example, display 110 as shown in FIG. 1 and/or display 304 shown in FIG. 3. This display may allow a user to ensure that end-effector 602 is in a desirable position in relation to robot arm 604, robot base 610, the patient, and/or the user.

For example, as shown in FIG. 7A, markers 702 may be placed around the surface of end-effector 602 so that a tracking device placed away from the surgical field and facing toward the robot and surgical field is able to view at least 3 of the markers 702 through a range of common orientations of the end effector relative to the tracking device. For example, distribution of markers in this way allows end-effector 602 to be monitored by the tracking devices when end-effector 602 is rotated by +/−135 degrees about the z-axis of the surgical robot system.

In addition, in exemplary embodiments, end-effector 602 may be equipped with infrared (IR) receivers that can detect when an external camera is getting ready to read markers 702. Upon this detection, end-effector 602 may then illuminate markers 702. The detection by the IR receivers that the external camera is ready to read markers 702 may signal the need to synchronize a duty cycle of markers 702, which may be light emitting diodes, to an external camera. This may also allow for lower power consumption by the robotic system as a whole, whereby markers 702 would only be illuminated at the appropriate time instead of being illuminated continuously. Further, in exemplary embodiments, markers 702 may be powered off to prevent interference with other navigation tools, such as different types of surgical instruments.

FIG. 8A depicts instrument 608 and instrument assembly 802. Instrument assembly 802 may further comprise tracking array 612, markers 804, an outer sleeve 806, one or more grooves 808, a tip 810, and an opening 812. Instrument 608 may include tip 814. Ultimately, as explained in greater detail with respect to FIGS. 10A and 10B, instrument assembly 802, which may house instrument 608, may be inserted into guide tube 606.

Markers 804 may be of any type described herein including but not limited to light emitting diodes or reflective spheres. Markers 804 are monitored by tracking devices associated with the surgical robot system and may be one or more line of sight cameras. The cameras may track the location of instrument assembly 802 based on the position and orientation of tracking array 612 and markers 804. A user, such as a surgeon, may orient instrument assembly 612 in a manner so that tracking array 612 and markers 804 are sufficiently recognized by the tracking devices to display instrument assembly 802 and markers 804 on, for example, display 110 of the exemplary surgical robot system. The manner in which a surgeon may place instrument assembly 802 into guide tube 606 and adjust instrument assembly 802 is explained in greater detail below.

Instrument assembly 802 may also include outer sleeve 806. Outer sleeve 806 may contain one or more grooves 808 and tip 810. As explained in greater detail below, tip 810 may contain lead-in features that assist in lining up one of grooves 808 with certain features of guide tube 606 to orient instrument assembly 802. The manner in which a user inserts instrument assembly 802 into guide tube 606 is explained in further detail with respect to FIGS. 10A and 10B.

Figure 8B:
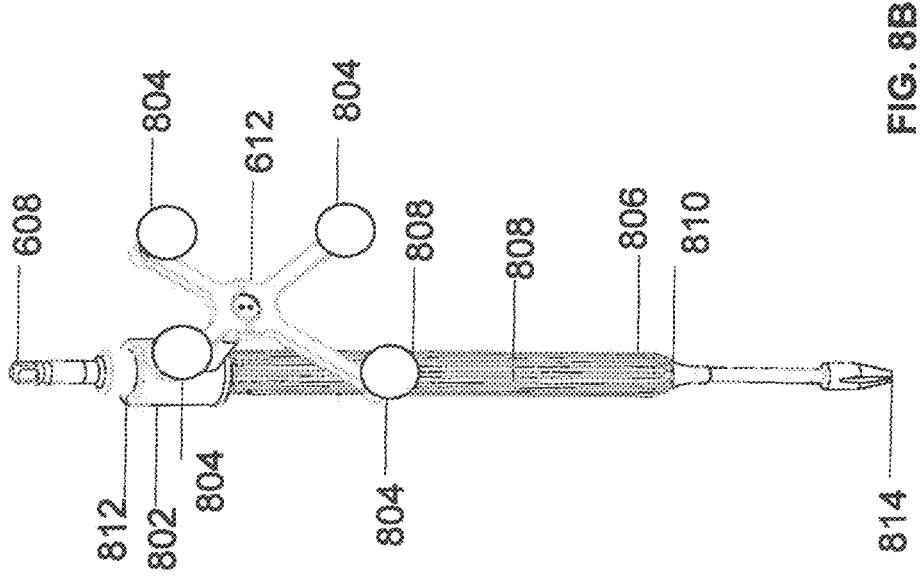

FIG. 8A also depicts instrument 608. Instrument 608 may be a surgical tool or implement associated with the surgical robot system. Instrument 608 may be inserted into instrument assembly 802 by inserting tip 814 into opening 812. Once inside instrument assembly 802, instrument 608 is free to rotate about its shaft axis and move in an axial direction as determined by the user. FIG. 8B depicts instrument 608 inserted into instrument assembly 802. FIG. 8C depicts a bottom view of instrument 608 inserted into instrument assembly 802.

Figure 9B:
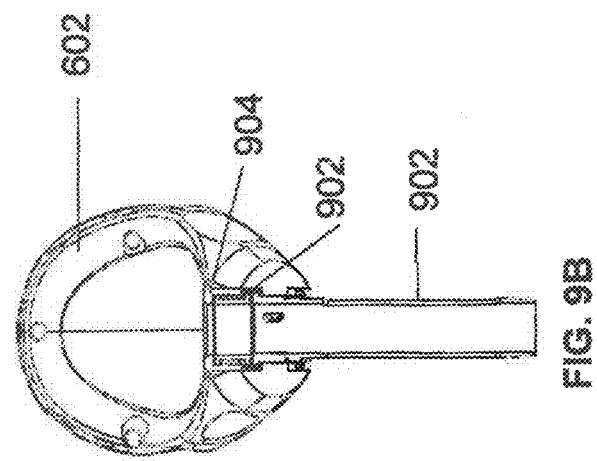
FIGS. 9A-B illustrate an end-effector in accordance with an exemplary embodiment.
Figure 9A:
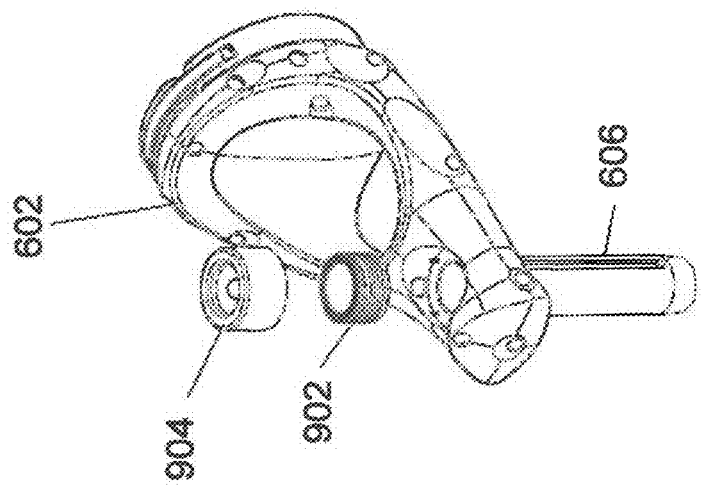

FIGS. 9A and 9B illustrate end-effector 602 consistent with an exemplary embodiment. End-effector 602 may comprise sensor 902 and sensor cover 904. The surgical robot system may contain circuitry that is configured to restrict or prevent robot arm 604 from moving when an instrument (for example, instrument 608) is in guide tube 606. Restricting or preventing movement of robot arm 604 while instrument 608 or another surgical instrument is in guide tube 606 may prevent a potentially hazardous situation to the patient and/or the user of the system while a sharp instrument is engaged in guide tube 606.

Sensor 902 may be configured such that it detects the presence of an instrument in guide tube 606. As shown in FIGS. 9A and 9B, sensor 902 may be embedded in an upper portion of guide tube 606. Sensor 902 may be a hall effect sensor using magnetic properties of the instrument to detect the instrument's presence in guide tube 606. Sensor 902 may be covered by sensor cover 904 as shown in FIGS. 9A and 9B.

Sensor 902 may detect the instrument's presence in guide tube 606. By way of example and in no way intended to limit the manner in which the sensor may be implemented, sensor 902 may be a capacitive or resistive sensor which uses changes in the electrical properties of guide tube 606, such as its impedance, when an instrument is present in guide tube 606. Further, sensor 902 may be a mechanical switch, such as an actuated or strain gauge. Further still, sensor 902 may be an optical sensor to determine the presence of an instrument in guide tube 606. In addition, sensor 902 may be an inductive sensor that uses magnetic field changes to determine the presence of an instrument in guide tube 606.

Sensor 902 may be configured to send a signal (sensor signal) to circuitry associated with the surgical robot system. Once the surgical robot system receives such a sensor signal, surgical robot system may restrict or prevent movement of robot arm 604 while an instrument is inside guide tube 606.

In a further embodiment, the surgical robot system may also disable tracking markers 702 in response to the sensor signal. This disabling response would prevent the undesirable situation of optical interference and partial occlusion from tracking markers 702, particularly if tracking markers are light emitting diodes.

FIGS. 10A and 10B illustrate a top view of end-effector 602 while instrument assembly 802 is inside guide tube 606 consistent with an exemplary embodiment. End-effector 602 may further comprise spring 1002 and ball detent 1004, both of which may be disposed in or near guide tube 606. FIGS. 10A and 10B also depict outer sleeve 806 and grooves 808.

Figure 13:
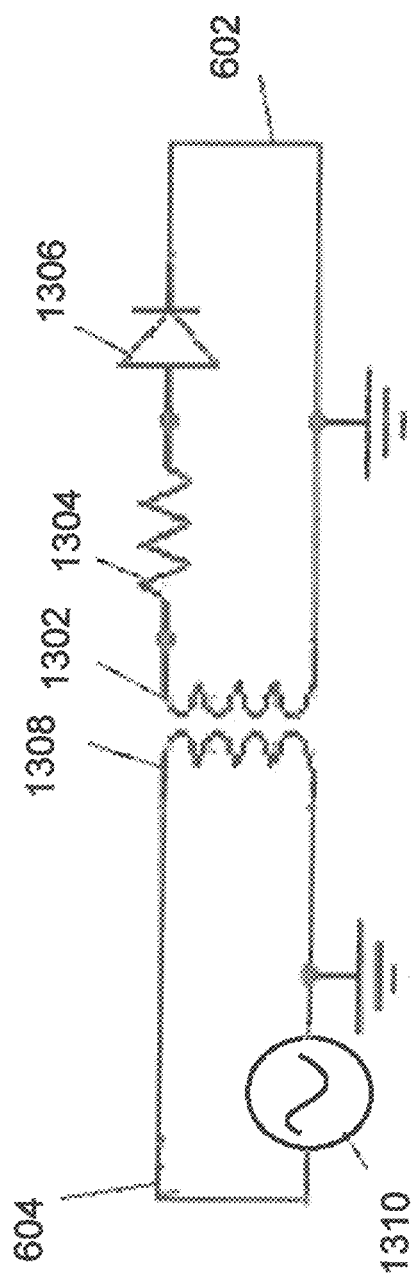
FIG. 13 illustrates portions of an end-effector and robot arm in accordance with an exemplary embodiment.

Instrument 608 may be disposed within instrument assembly 802 as described with respect to FIG. 13. While instrument 608 is disposed in instrument assembly 802, instrument assembly 802 may be inserted in guide tube 606. Guide tube 606 may restrict the movement of instrument assembly 802 in a manner such that tracking array 612 remains in essentially the same orientation relative to robot arm 604 and robot base 612 so that tracking devices can display the location of instrument assembly 802 on, for example, display 110. Instrument 608 may be free to rotate about its shaft without affecting rotation of the array and may move in a direction consistent with trajectory 614.

Specifically, instrument assembly 802 (after instrument 608 is inserted therein), may be inserted into guide tube 606. Structures on tip 810 of outer sleeve 806 may cause one of grooves 808 to line up and engage with ball detent 1004. Ball detent 1004 may be in communication with spring 1002 such that when a force is applied to ball detent 1004, it is able to move backward against spring 1002 and when the force is removed spring 1002 moves ball detent 1004 in a forward direction. When ball detent 1004 engages a groove 808 it may move forward into that groove 808 and spring 1002 may apply sufficient force on ball detent 1004 so that ball detent is biased towards that groove 808. With ball detent 1004 lined up and engaged with one of grooves 808, instrument assembly 802 is inserted further into guide tube 606. FIG. 10B depicts a groove 808 engaged with ball detent 1004.

Instrument 608 may freely rotate about its shaft and move along the path of trajectory 614 within instrument assembly 802. Instrument assembly 802 may be restricted from rotating within guide tube 606 while a groove 808 is engaged with ball detent 1004. The rotational position of instrument assembly 802 within guide tube 606 may be chosen such that tracking array 612 is adequately visible to the tracking devices in order to properly display the position of instrument 608 on, for example, display 110 of the surgical robot system.

While rotational movement of instrument assembly 802 inside guide tube 606 may be restricted, the rotational position of instrument assembly 802 may be adjusted. For example, instrument assembly 802 may be adjusted so that tracking array 612 is in a better position to be visible by the tracking devices. In an exemplary embodiment, sufficient rotational force may be applied to instrument assembly 802 to disengage ball detent 1004 from a groove 808. Ball detent 1004 may move backwards upon disengaging with a groove 808. This disengagement is depicted in FIG. 10A. Once disengaged, the rotational position of instrument assembly 802 may be adjusted so that ball detent 1004 moves forward and engages a different groove 808.

Ball detent 1004 and the one or more grooves 808 may be configured such that movement along the path of trajectory 614 is not restricted. This configuration may allow instrument assembly 802 to move along a path of trajectory 614, while guide tube 606 restricts rotational movement of instrument assembly 802 to maintain a fixed orientation of tracking array 612 in relation to the tracking devices.

Ball detent 1004 has been described in relation to spring 1002 and being a spring plunger type of structure. However, it is understood that other structures may be used to restrict rotational movement of instrument assembly 802 in guide tube 606 in order to maintain an orientation of tracking array 612. For example, such structures may include and are not limited to a coil spring, wave spring, flexture, torsional spring mounted to a lever, or a compressible material. Further, ball detent 1004 and spring 1002 have been described as being part of guide tube 606, however, ball detent 1004 and spring 1002 may be disposed on instrument assembly 802 and engage with complimentary mechanisms associated with end-effector 602 or guide tube 606 to similarly restrict the rotation movement of instrument assembly 802.

Figure 11:
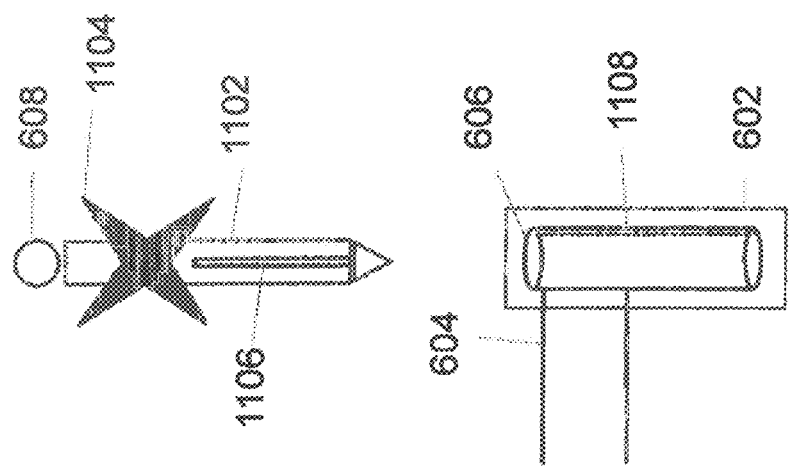
FIG. 11 illustrates an instrument and guide tube in accordance with an exemplary embodiment.

FIG. 11 illustrates end-effector 602, instrument 608, instrument assembly 1102, tracking array 1104, and guide tube 606 consistent with an exemplary embodiment. Instrument assembly 1102 may further comprise groove 1106. Guide tube 606 may further comprise channel 1108.

As described previously, rotational movement of instrument assembly 802 may be restricted when it is received by guide tube 606. In an exemplary embodiment to restrict movement of an instrument assembly while inside a guide tube, instrument assembly 1102 may have groove 1106 configured to engage channel 1108 of guide tube 606 to similarly restrict rotational movement of instrument assembly 1102 when received by guide tube 606. Once groove 1106 is engaged with channel 1108, instrument assembly 1102 is restricted from rotating about its shaft axis while instrument assembly 1102 is inside guide tube 606.

Other methods and components may be used to restrict the rotational movement of an instrument assembly while inside a guide tube. For example, one or more cylindrical rollers may be used that is configured with roller axis perpendicular to the instrument shaft to roll and allow for axial movement of an instrument assembly along the path of trajectory 614 but is configured to remain stationary when attempts are made to rotationally move instrument assembly within guide tube 606. This configuration would have the effect of fixing the orientation of tracking array 612. The roller may be made of a flexible material and held rigidly protruding into guide tube 606 to engage with an outer sleeve of the instrument assembly. The roller may also be made of a rigid material and spring loaded, pushing into guide tube 606 to engage with the instrument assembly. Moreover, the roller may be disposed on an instrument assembly and engage guide tube 606 when the instrument assembly is inserted into guide tube 606.

As another exemplary embodiment, rotation of an outer sleeve of instrument assembly may be restricted from rotating but allowing for axial movement through the use of anisotropic surface textures for the outer sleeve and guide tube 606. This texture pattern may allow for different friction forces associated with rotation of the outer sleeve and axial movement so that a user may need to apply a relatively higher force to rotationally move the instrument assembly compared to moving the instrument assembly in an axial direction consistent with trajectory 614.

Figure 12:
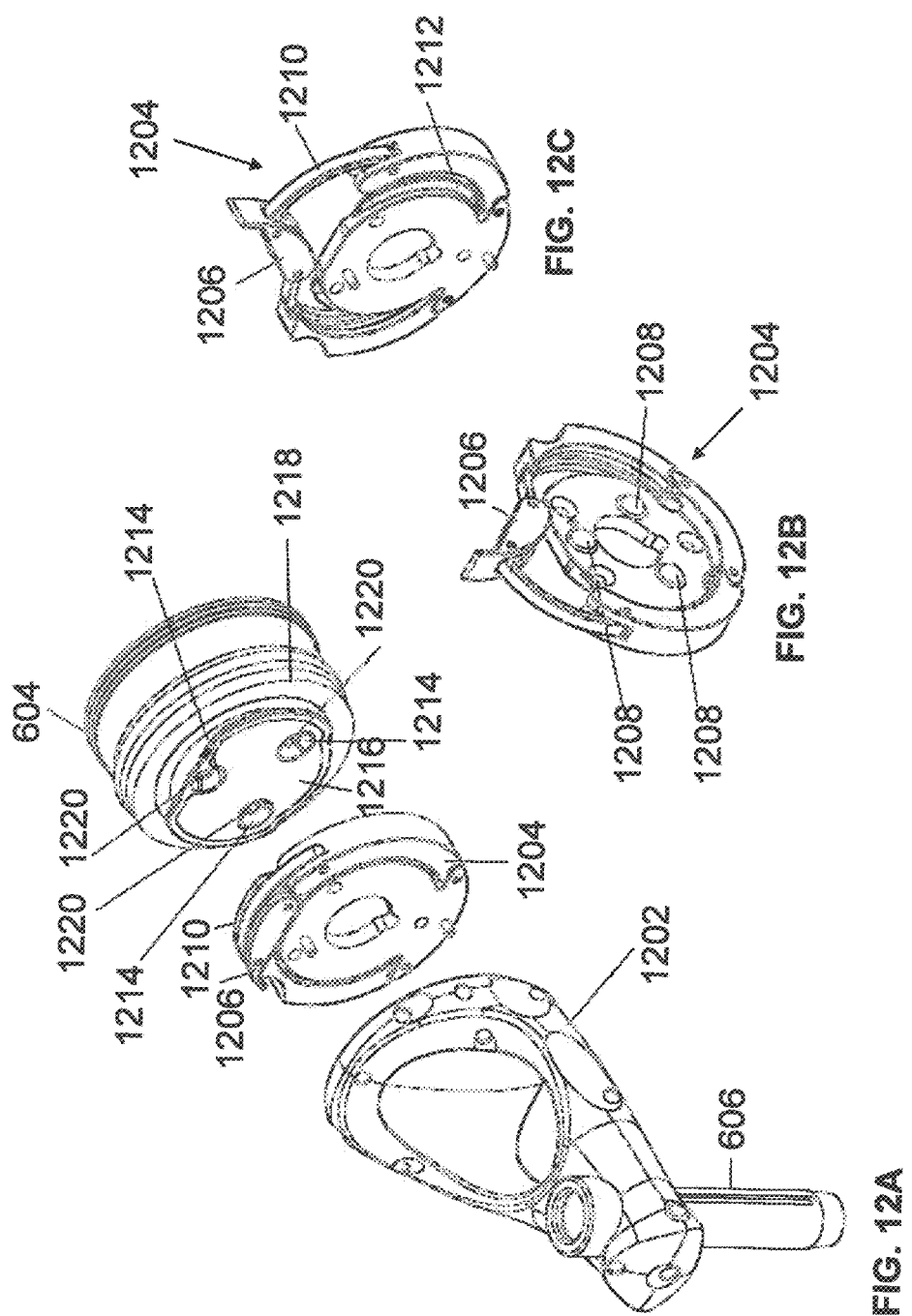
FIGS. 12A-C illustrate portions of an end-effector and robot arm in accordance with an exemplary embodiment.

FIGS. 12A-C illustrate end-effector 602 and a portion of robot arm 604 consistent with an exemplary embodiment. End-effector 602 may further comprise body 1202 and clamp 1204. Clamp 1204 may comprise handle 1206, balls 1208, spring 1210, and lip 1212. Robot arm 604 may further comprise depressions 1214, mounting plate 1216, lip 1218, and magnets 1220.

End-effector 602 may mechanically interface and/or engage with the surgical robot system and robot arm 604 through one or more couplings. For example, end-effector 602 may engage with robot arm 604 through a locating coupling and/or a reinforcing coupling. Through these couplings, end-effector 602 may fasten with robot arm 604 outside a flexible and sterile barrier. In an exemplary embodiment, the locating coupling may be a magnetically kinematic mount and the reinforcing coupling may be a five bar over center clamping linkage.

With respect to the locating coupling, robot arm 1002 may comprise mounting plate 1716, which may be non-magnetic material, one or more depressions 1214, lip 1218, and magnets 1220. Magnet 1220 is mounted below each of depressions 1214. Portions of clamp 1204 may comprise magnetic material and be attracted by one or more magnets 1220. Through the magnetic attraction of clamp 1204 and robot arm 604, balls 1208 become seated into respective depressions 1214. For example, balls 1208 as shown in FIG. 12B would be seated in depressions 1214 as shown in FIG. 12A. This seating may be considered a magnetically-assisted kinematic coupling. Magnets 1220 may be configured to be strong enough to support the entire weight of end-effector 602 regardless of the orientation of end-effector 602. The locating coupling may be any style of kinematic mount that uniquely restrains six degrees of freedom.

With respect to the reinforcing coupling, portions of clamp 1204 may be configured to be a fixed ground link and as such clamp 1204 may serve as a five bar linkage. Closing clamp handle 1206 may fasten end-effector 602 to robot arm 604 as lip 1212 and lip 1218 engage clamp 1204 in a manner to secure end-effector 602 and robot arm 604. When clamp handle 1206 is closed, spring 1210 may be stretched or stressed while clamp 1204 is in a locked position. The locked position may be a position that provides for linkage past center. Because of a closed position that is past center, the linkage will not open absent a force applied to clamp handle 1206 to release clamp 1204. Thus, in a locked position end-effector 602 may be robustly secured to robot arm 604.

Spring 1210 may be a curved beam in tension. Spring 1210 may be comprised of a material that exhibits high stiffness and high yield strain such as Virgin PEEK (polyether-ether-ketone). The linkage between end-effector 602 and robot arm 604 may provide for a sterile barrier between end-effector 602 and robot arm 604 without impeding fastening of the two couplings.

The reinforcing coupling may be a linkage with multiple spring members. The reinforcing coupling may latch with a cam or friction based mechanism. The reinforcing coupling may also be a sufficiently powerful electromagnet that will support fastening end-effector 102 to robot arm 604. The reinforcing coupling may be a multi-piece collar completely separate from either end-effector 602 and/or robot arm 604 that slips over an interface between end-effector 602 and robot arm 604 and tightens with a screw mechanism, an over center linkage, or a cam mechanism.

FIG. 13 is a circuit diagram that illustrates power transfer between end-effector 602 and robot arm 604 consistent with an exemplary embodiment. End-effector 602 may comprise a coil 1302, resistor 1304, and diode 1306. Robot arm 604 may comprise coil 1308 and voltage supply 1310.

End-effector 602 and robot arm 604 may be configured in a manner to allow for wireless power transfer in order to power end-effector 602 and components associated with end-effector 602. In an exemplary embodiment, end-effector 602 may comprise coil 1302 that receives an electromagnetic field generated by robot arm 604. Robot arm 604 may contain coil 1308, which may serve as a primary coil in an inductive power transfer system between robot arm 604 and end-effector 602 over an air gap. In an exemplary embodiment, the air gap may be in the range of 0.1-20 mm. Coil 1308 may be coupled to voltage supply 1310 in order to generate the electromagnetic field. The electromagnetic field may be received by coil 1304 of end-effector 602 to generate an electrical current.

The inductive power relationship between may power components of end-effector 602 such as tracking markers 702, sensor 902, and other electrical components associated with end-effector 602. By providing wireless powering, end-effector 602 may be physically and/or electrically isolated from robot arm 604 while powering electronics and other components contained in end-effector 602.

The resistance of resistor 1304 may be varied among a number of distinct states, causing differential power draw. The power draw may be measured from the side of the surgical robot as a means of wirelessly passing a signal from end-effector 602 to the surgical robot base 610. Alternatively, a battery could be used to power the electronics, and a standard wireless communications protocol such as Bluetooth may be used to exchange signals between end-effectuator 602 and robot base 612. Data transferred to robot base 612 may include state information. This information may include a determination of whether end-effector 602 is detached from robot arm 604, and if instrument 608 is present in guide tube 606.

The power transmission between robot arm 604 and end-effector 602 may be based on electromagnetism, optics, or ultrasound. For each of these transmission types, the corresponding resistance on end-effector 602 can be varied to communicate the state of end-effector 602. End-effector 602 may propagate power or receive one or more signals by any of the aforementioned principles to other items in the sterile field, such as drills, screw drivers, implant holders, or lights. In addition, power and/or signal may be passed to other sterile items via a contact connection.

Figure 14:
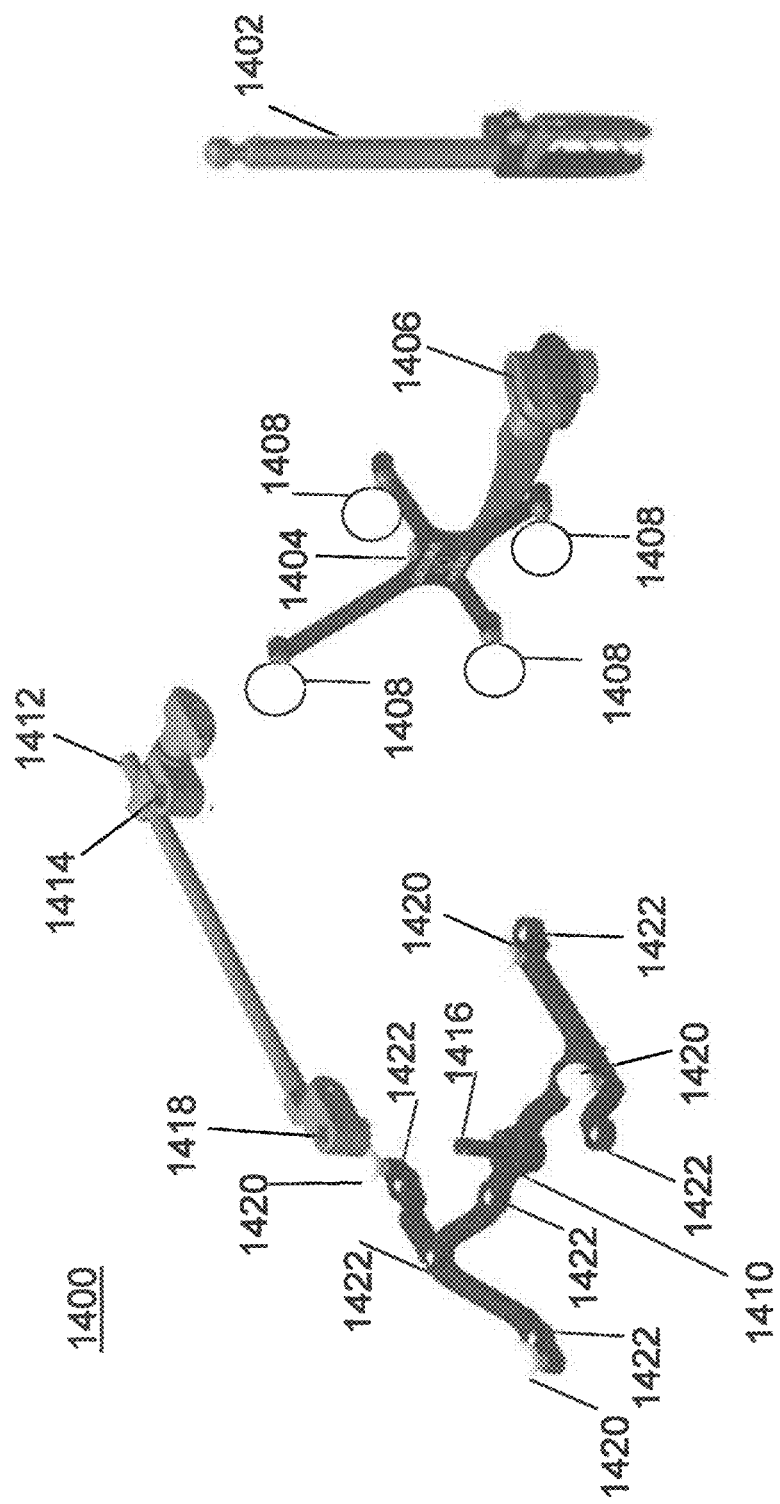
FIG. 14 illustrates a dynamic reference array, an imaging array, and other components in accordance with an exemplary embodiment.
Figure 15:
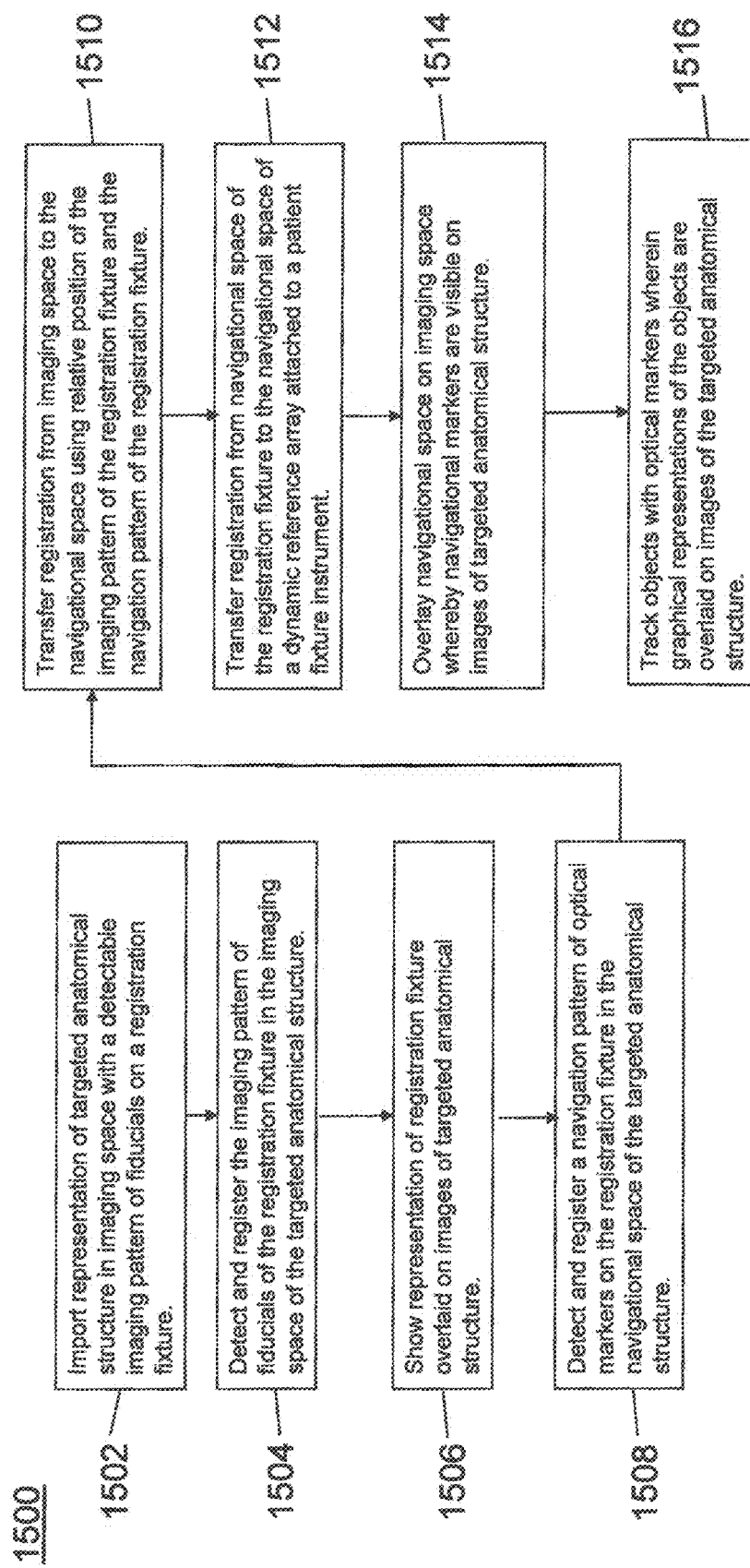
FIG. 15 illustrates a method of registration in accordance with an exemplary embodiment.

Referring to FIGS. 14 and 15, prior to or during a surgical procedure, certain registration procedures may be conducted in order to track objects and a target anatomical structure of the patient both in a navigation space and an image space. In order to conduct such registration, a registration system 400 may be used as illustrated in FIG. 14.

A patient fixation instrument 1402 may be secured to a rigid anatomical structure of the patient and a dynamic reference base (DRB) 1404 may be attached to patient fixation instrument 1402. For example, patient fixation instrument 1402 may be inserted into opening 1406 of dynamic reference base 1404. Dynamic reference base 1404 may contain markers 1408 that are visible to tracking devices, such as tracking subsystem 532. These markers may be optical markers or reflective spheres as previously discussed herein.

Patient fixation instrument 1402 is attached to a rigid anatomy of the patient and may remain attached throughout the surgical procedure. In an exemplary embodiment, patient fixation instrument 1402 is attached to a rigid area of the patient, for example a bone, that is located away from the targeted anatomical structure subject to the surgical procedure. In order to track the targeted anatomical structure, dynamic reference base 1404 is associated with the targeted anatomical structure through the use of a registration fixture that is temporarily placed on or near the targeted anatomical structure in order to register the dynamic reference base with the location of the targeted anatomical structure.

A registration fixture 1410 is attached to patient fixation instrument 1402 through the use of a pivot arm 1412. Pivot arm 1412 is attached to patient fixation instrument 1402 by inserting patient fixation instrument 1402 through an opening 1414 of registration fixture 1410. Pivot arm 1412 is attached to registration fixture 1410 by, for example, inserting a knob 1416 through an opening 1418 of pivot arm 1412.

Using pivot arm 1412, registration fixture 1410 may be placed over the targeted anatomical structure and its location may be determined in an image space and navigation space using tracking markers or fiducials on registration fixture 1410. Registration fixture 1410 may contain a collection of markers 1420 that are visible in a navigational space (for example, markers 1420 may be detectable by tracking subsystem 532). Markers 1420 may be optical markers visible in infrared light as previously described herein. Registration fixture 1410 may also contain a collection of fiducials 1422, for example bearing balls, that are visible in an imaging space (for example, a three dimension CT image). As described in greater detail with respect to FIG. 15, using registration fixture 1410, the targeted anatomical structure may be associated with dynamic reference base 1404 thereby allowing depictions of objects in the navigational space to be overlaid on images of the anatomical structure. Dynamic reference base 1404, located at a position away from the targeted anatomical structure, may become a reference point thereby allowing removal of registration fixture 1410 and/or pivot arm 1412 from the surgical area.

FIG. 15 provides an exemplary method 1500 for registration consistent with the present disclosure. Method 1500 begins at step 1502 wherein a graphical representation (or image(s)) of the targeted anatomical structure may be imported into system 300, for example computer 408. The graphical representation may be three dimensional CT or a fluoroscope scan of the targeted anatomical structure of the patient which includes registration fixture 1410 and a detectable imaging pattern of fiducials 1420.

At step 1504, an imaging pattern of fiducials 1420 is detected and registered in the imaging space and stored in computer 408. Optionally, at this time at step 1506, a graphical representation of the registration fixture may be overlaid on the images of the targeted anatomical structure.

At step 1508, a navigational pattern of registration fixture 1410 is detected and registered by recognizing markers 1420. Markers 1420 may be optical markers that are recognized in the navigation space through infrared light by tracking subsystem 532 via position sensor 540. Thus, the location, orientation, and other information of the targeted anatomical structure is registered in the navigation space. Therefore, registration fixture 1410 may be recognized in both the image space through the use of fiducials 1422 and the navigation space through the use of markers 1420. At step 1510, the registration of registration fixture in the image space is transferred to the navigation space. This transferal is done, for example, by using the relative position of the imaging pattern of fiducials 1422 compared to the position of the navigation pattern of markers 1420.

At step 1512, registration of the navigation space of registration fixture (having been registered with the image space) is further transferred to the navigation space of dynamic registration array 1404 attached to patient fixture instrument 1402. Thus, registration fixture 1410 may be removed and dynamic reference base 1404 may be used to track the targeted anatomical structure in both the navigation and image space because the navigation space is associated with the image space.

At steps 1514 and 1516, the navigation space may be overlaid on the image space and objects with markers visible in the navigation space (for example, surgical instruments with optical markers). The objects may be tracked through graphical representations of the surgical instrument on the images of the targeted anatomical structure.

Although several embodiments of the invention have been disclosed in the foregoing specification, it is understood that many modifications and other embodiments of the invention will come to mind to which the invention pertains, having the benefit of the teaching presented in the foregoing description and associated drawings. It is thus understood that the invention is not limited to the specific embodiments disclosed hereinabove, and that many modifications and other embodiments are intended to be included within the scope of the appended claims. Moreover, although specific terms are employed herein, as well as in the claims which follow, they are used only in a generic and descriptive sense, and not for the purposes of limiting the described invention, nor the claims which follow.

It will be appreciated by those skilled in the art that while the invention has been described above in connection with particular embodiments and examples, the invention is not necessarily so limited, and that numerous other embodiments, examples, uses, modifications and departures from the embodiments, examples and uses are intended to be encompassed by the claims attached hereto. The entire disclosure of each patent and publication cited herein is incorporated by reference, as if each such patent or publication were individually incorporated by reference herein. Various features and advantages of the invention are set forth in the following claims.

The invention claimed is:

1. A surgical robot system comprising:
a robot base having a display;
a robot arm coupled to the robot base, wherein movement of the robot arm is electronically controlled by the robot base; and
an end-effector, coupled to the robot arm, containing one or more end-effector tracking markers;
wherein the robot base is in electronic communication with the robot arm and the end effector,
wherein the one or more end-effector tracking markers are configured to be detected by a camera system and the display is configured to indicate a location of the end-effector in relation to at least one of the robot base and the robot arm,
wherein the robot arm is configured to selectively move the end-effector along the x, y, and z axes and configured for selective rotation about one of the x, y, and z axes,
wherein the robot arm does not provide six degrees of freedom,
wherein the robot arm is configured to position the end-effector in location to optimize the placement of pedicle screws.

2. The surgical robot system of claim 1, wherein the markers are positioned around the surface of end-effector.

3. The surgical robot system of claim 1, wherein the distribution of the markers enables the end-effector to be monitored when the end-effector is rotated by 135 degrees about a z-axis.

4. A surgical robot system comprising:
a robot base having a display;
a robot arm coupled to the robot base, wherein movement of the robot arm is electronically controlled by the robot base; and
an end-effector, coupled to the robot arm, containing one or more end-effector tracking markers;
wherein the robot base is in electronic communication with the robot arm and the end effector,
wherein the one or more end-effector tracking markers are configured to be detected by a camera system and the display is configured to indicate a location of the end-effector in relation to at least one of the robot base and the robot arm,
wherein the robot arm is configured to selectively move the end-effector along the x, y, and z axes, wherein the robot arm does not provide six degrees of freedom,
wherein the robot arm is configured to position the end-effector in location to optimize the placement of pedicle screws.

* * * * *